United States Patent
Kim et al.

(10) Patent No.: US 9,920,016 B2
(45) Date of Patent: *Mar. 20, 2018

(54) PROCESS FOR THE PREPARATION OF 4-AMINO 1-((1S,4R,5S)-2-FLUORO-4,5-DIHYDROXY-3-HYDROXYMETHYL-CYCLOPENT-2-ENYL)-1H-PYRIMIDIN-2-ONE

(71) Applicant: Rexahn Pharmaceuticals, Inc., Rockville, MD (US)

(72) Inventors: Deog Joong Kim, Rockville, MD (US); Haifeng Yin, Shanghai (CN); Eliezer Falb, Givatayim (IL); Leigh Andre Pearcey, Didcot (GB); Jonathan Cummins, Didcot (GB); Petra Dieterich, Abingdon (GB); Jean-Francois Carniaux, Abingdon (GB); Yi Wang, Chester Springs, PA (US); Vikram Chandrakant Purohit, Downingtown, PA (US)

(73) Assignee: REXAHN PHARMACEUTICALS, INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/379,553

(22) Filed: Dec. 15, 2016

(65) Prior Publication Data
US 2017/0158662 A1    Jun. 8, 2017

Related U.S. Application Data

(63) Continuation of application No. 14/845,968, filed on Sep. 4, 2015, now Pat. No. 9,533,958, which is a continuation of application No. 14/216,242, filed on Mar. 17, 2014, now Pat. No. 9,150,520.

(60) Provisional application No. 61/800,475, filed on Mar. 15, 2013.

(51) Int. Cl.
| C07D 239/47 | (2006.01) |
| C07F 7/18 | (2006.01) |
| C07D 317/44 | (2006.01) |
| C07D 405/04 | (2006.01) |
| C07D 317/22 | (2006.01) |

(52) U.S. Cl.
CPC ......... *C07D 239/47* (2013.01); *C07D 317/22* (2013.01); *C07D 317/44* (2013.01); *C07D 405/04* (2013.01); *C07F 7/1892* (2013.01)

(58) Field of Classification Search
CPC .................. C07D 317/44; C07D 239/47
See application file for complete search history.

(56) References Cited

U.S. PATENT DOCUMENTS

| 4,820,508 | A | 4/1989 | Wortzman | |
| 4,938,949 | A | 7/1990 | Borch et al. | |
| 7,405,214 | B2* | 7/2008 | Lee | A61K 31/513 |
| | | | | 514/247 |
| 9,150,520 | B2* | 10/2015 | Yin | C07D 239/47 |
| 9,533,958 | B2* | 1/2017 | Yin | C07D 239/47 |
| 2005/0222185 | A1* | 10/2005 | Ahn | A61K 31/513 |
| | | | | 514/269 |
| 2014/0275537 | A1* | 9/2014 | Yin | C07D 239/47 |
| | | | | 544/317 |
| 2017/0014411 | A1* | 1/2017 | Lee | A61K 39/00 |
| 2017/0158662 | A1* | 6/2017 | Kim | C07D 239/47 |

FOREIGN PATENT DOCUMENTS

| JP | 2007-531736 A | 11/2007 |
| WO | WO-2005/097757 A2 | 10/2005 |
| WO | WO-2005/097757 A3 | 12/2005 |

OTHER PUBLICATIONS

H.R. Moon et al., 14 Bioorganic & Medicinal Chemistry Letters, 5641-5644 (2004).*
Agarwal, H. K.; Buckheit, K. W.; Buckheit, R. W.; Parang, K. Bioorganic & Medicinal Chemistry Letters, 2012, 22(17), 5451-5454.
Akella, Lakshmi B.; Vince, Robert From Tetrahedron (1996), 52(25), 8407-8412.
Baldwin, S.A.; Mackey, J.R.; Cass, C.E.; Young, J.D. Mol. Med. Today 1999, 5, 216.
Balzarini, J.; Baba, M., Pauwels, R., Herdewijn, P., De Clercq, E. Biochem. Pharmacol. 1988, 37, 2847.
Biggadike, K. Borthwick A.D. J. Chem. Soc., Chem. Commun. 1990, 1380.
Choi et al., "Fluorocyclopentenyl-cytosine with Broad Spectru, and Potent Anitumor Activity +," Journal of Medicinal Chemistry, vol. 55, May 2012, pp. 4521-4525.

(Continued)

*Primary Examiner* — Alexander R Pagano
(74) *Attorney, Agent, or Firm* — Venable LLP; Keith G. Haddaway; Annette K. Kwok

(57) ABSTRACT

Processes for the preparation of 4-amino-1-((1S,4R,5S)-2-fluoro-4,5-dihydroxy-3-hydroxymethyl-cyclopent-2-enyl)-1H-pyrimidin-2-one(13, RX-3117) and its intermediates are described.

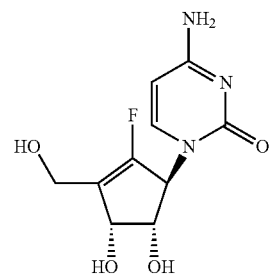

16 Claims, No Drawings

(56) References Cited

OTHER PUBLICATIONS

Choi, W. J. et al. Nucleosides, Nucleotides, and Nucleic Acids, 2005, 24(5-7), 611-613.
Chong, Y.; Gumina, G.; Chu, C. K. Tetrahedron: *Asymmetry*, 2000, 11, 4853.
Chu, C.K. et al. Antimicrob. Agents Chemother., 1995, 6, 979.
Crimmins, M. T. Tetrahedron, 1998, 54, 9229.
Giessrigl, B. et al. Human Molecular Genetics, 2012, 21(21), 4615-4627.
Gumina, G.; Chong, Y.; Choi, Y. Chu, C. K. Org. Lett., 2000, 2, 1229.
Hertel, L.W.; Kroin, J.S.; Misner, J.W.; Tustin, J.M. J. Org. Chem. 1988, 53, 2406.
International Search Report and Written Opinion issued in International Application No. PCT/US2014/030635 dated Jun. 4, 2014.
Jeong, L. S. et al. J. Med. Chem., 2003, 46, 201.
Jeong, L. S. et al. Nucleosides, Nucleotides, and Nucleic Acids, 2007, 26, 713-716.
Kumamoto, H. et al., European Journal of Organic Chemistry, 2685-2691 (2011).
Li, W.; Yin, X.; Schneller, S. W. Bioorg. Med. Chem. Lett. 2008, 18, 220.
Madhavan, G. V. B.; McGee, D. P.C.; Rydzewski, R. M.; Boehme, R.; Martin, J. C.; Prisbe, E. J. Med. Chem., 1988, 31, 1798.
Moon et al., "Synthesis of 5'-substituted fluoro-neplanocin A analogues: importance of a hydrogen bonding donor at 5'-position for the inhibitory activity of S-adenosylhomocysteine hydrolase," Bioorganic & Medicinal Chemistry Letters, vol. 14, 2004, 5641-5644.
Okabe, M.; Sun, R.-C; Zenchoff, G.B. J. Org. Chem. 1991, 56, 4392.
Payne, A. N.; Roberts, S. M. J. Chem. Soc., Perkin Trans. 1, 1992, 2633.
Plunkett, W.; Huang, P.; Ganghi, V. Nucleosides Nucleotides, 1997, 16, 1261.
Prichard, Mark N.; Antiviral Research, 2006, 71(1), 1-6.
Schachter, J.B.; Yasuda, R.P.; Wolfe, B.B. Cell Signaling 1995, 7, 659.
Shryock, J.C.; Belardinelli, L. Am. J. Cardiol. 1997, 79, 2.
Wachtmeister, J.; Muhlman, A.; Classon, B., Samuelsson B. Tetrahedron 1999, 55, 10761.
Wiebe, L. I. et al. Current Radiopharmaceuticals, 2012, 5(1), 38-46.
Yamashita, M.; Kato, Y.; Suzuki, K.; Reddy, P.M.; Oshikawa, T. Abstracts of 29th Congress of Heterocyclic Chemistry, 1998, 461.
Yin. X.-Q.; Schneller, S. W. Tetrahedron Lett., 2005, 46, 7535.
Yokoyama, M. Synthesis, 2000, 1637.
Yokoyama, M.; Momotake, A. Synthesis, 1999, 1541.
Yoshimura Y.; Saitoh, K.; Ashida, N.; Sakata S.; Matsuda, A. Bioorganic Med. Chem. Lett., 1994, 4, 721.
Zhao, L. X. et al., 49 Nucleic Acids Symposium Series, 107-108 (2005).
Choi et al., "Fluorocyclopentenyl-cytosine with Broad Spectrum and Potent Antihumor Activity," Journal of Medicinal Chemistry, vol. 55, No. 9, pp. 4521-4525 (2012).

\* cited by examiner

PROCESS FOR THE PREPARATION OF 4-AMINO 1-((1S,4R,5S)-2-FLUORO-4,5-DIHYDROXY-3-HYDROXYMETHYL-CYCLOPENT-2-ENYL)-1H-PYRIMIDIN-2-ONE

This application is a continuation of U.S. patent application No. U.S. patent application Ser. No. 14/845,968, filed on Sep. 4, 2015, which is a continuation of U.S. patent application Ser. No. 14/216,242, filed on Mar. 17, 2014, which claims the benefit of U.S. Provisional Application No. 61/800,475, filed Mar. 15, 2013, which are hereby incorporated by reference in its entirety.

FIELD OF THE INVENTION

The present invention relates to the process for the preparation of 4-amino-1-((1 S,4R,5S)-2-fluoro-4,5-dihydroxy-3-hydroxymethyl-cyclopent-2-enyl)-1H-pyrimidin-2-one and its intermediates.

BACKGROUND OF THE INVENTION

4-Amino-1-((1S,4R,5S)-2-fluoro-4,5-dihydroxy-3-hydroxymethyl-cyclopent-2-enyl)-1H-pyrimidin-2-one (RX-3117)

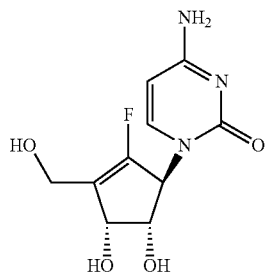

is disclosed in U.S. Pat. No. 7,405,214, which describes a synthetic method and method of treatment as well. The method described in U.S. Pat. No. 7,405,214 includes a total of 11 steps to synthesize the (3R,4R,6aR)-tert-Butyl-(5-fluoro-2,2-dimethyl-6-trityloxymethyl-4,6a-dihydro-3aH-cyclopenta[1,3]dioxol-4-yloxy)-diphenyl-silane from D-ribose, which is an important intermediate for the synthesis of 4-amino-1-((1S,4R,5S)-2-fluoro-4,5-dihydroxy-3-hydroxymethyl-cyclopent-2-enyl)-1H-pyrimidin-2-one. U.S. Pat. No. 7,405,214 uses an expensive catalyst which poses a challenge for implementation in plant production.

SUMMARY OF THE INVENTION

The present invention discloses a short route for the preparation of 4-amino-1-((1 S,4R,5S)-2-fluoro-4,5-dihydroxy-3-hydroxymethyl-cyclopent-2-enyl)-1H-pyrimidin-2-one through (3R,4R,6aR)-tert-butyl-(5-fluoro-2,2-dimethyl-6-trityloxymethyl-4,6a-dihydro-3aH-cyclopenta[1,3]dioxol-4-yloxy)-diphenyl-silane. Each step of the method is described individually and the invention can be considered as any one of the individual steps or any combination of steps taken together.

In embodiments, the invention is a process for the preparation of 4-amino-1-((1 S,4R,5S)-2-fluoro-4,5-dihydroxy-3-(hydroxymethyl)-cyclopent-2-en-1-yl)-pyrimidin-2(1H)-one (13) by reacting 4-amino-1-(3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one (12) with acid, for example HCl.

Embodiments of the process can include preparing 4-amino-1-(3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one (12) by reacting (3aR,4R,6aR)-5-fluoro-2,2-dimethyl-6-((trityloxy)methyl)-4,6a-dihydro-3aH-cyclopenta[d][1,3]dioxol-4-yl methanesulfonate (11) with cytosine.

Embodiments of the process can include preparing (3aR,4R,6aR)-5-fluoro-2,2-dimethyl-6-((trityloxy)methyl)-4,6a-dihydro-3aH-cyclopenta[d][1,3]dioxol-4-yl methanesulfonate (11) by reacting (3aS,4R,6aR)-5-fluoro-2,2-dimethyl-6-((trityloxy)methyl)-4,6a-dihydro-3aH-cyclopenta[d][1,3]dioxol-4-ol (10) with MsCl.

Embodiments of the process can include preparing (3aS,4R,6aR)-5-fluoro-2,2-dimethyl-6-((trityloxy)methyl)-4,6a-dihydro-3aH-cyclopenta[d][1,3]dioxol-4-ol (10) by deprotection of tert-butyl(((3aR,4R,6aR)-5-fluoro-2,2-dimethyl-6-((trityloxy)methyl)-4,6a-dihydro-3 aH-cyclopenta[d][1,3]dioxol-4-yl)oxy)diphenylsilane (9).

Embodiments of the process can include preparation of tert-butyl(((3aR,4R,6aR)-5-fluoro-2,2-dimethyl-6-((trityloxy)methyl)-4,6a-dihydro-3aH-cyclopenta[d][1,3]dioxol-4-yl)oxy)diphenylsilane (9) by reacting tert-butyl(((3aR,4R,6aR)-5-iodo-2,2-dimethyl-6-((trityloxy)methyl)-4,6a-dihydro-3aH-cyclopenta[d][1,3]dioxol-4-yl)oxy) diphenylsilane (8) with NFSI (N-fluorobenzenesulfonimide).

Embodiments of the process can include preparation of (3aS,4R,6aR)-5-fluoro-2,2-dimethyl-6-((trityloxy)methyl)-4,6a-dihydro-3aH-cyclopenta[d][1,3]dioxol-4-ol (9) by conversion of tert-butyl(((3aR,4R,6aR)-5-iodo-2,2-dimethyl-6-((trityloxy)methyl)-4,6a-dihydro-3aH-cyclopenta[d][1,3]dioxol-4-yl)oxy)diphenylsilane (8) to a boronic acid intermediate followed by hydrolysis and reaction with 1-chloromethyl-4-fluoro-1,4-diazoniabicyclo[2.2.2]octane bis(tetrafluoroborate) (Selectfluor®). In some embodiments The boronic acid intermediate is [(3aR,6S,6aR)-6-[tert-butyl(diphenyl)silyl]oxy-2,2-dimethyl-4-(trityloxymethyl)-6,6a-dihydro-3aH-cyclopenta[d][1,3]dioxol-5-yl]boronic acid (9c-1), and prepared by reaction of tert-butyl(((3aR,4R,6aR)-5-iodo-2,2-dimethyl-6-((trityloxy)methyl)-4,6a-dihydro-3aH-cyclopenta[d][1,3]dioxol-4-yl)oxy)diphenylsilane (8) with trimethylborate. In some embodiments, the boronic acid intermediate is [(3aR,6S,6aR)-2,2-dimethyl-5-(4,4,5,5-tetramethyl-1,3,2-dioxaborolan-2-yl)-4-(trityloxymethyl)-6,6a-dihydro-3aH-cyclopenta[d][1,3]dioxol-6-yl]oxy-tert-butyl-diphenyl-silane (9c-2), prepared by reacting tert-butyl(((3aR,4R,6aR)-5-iodo-2,2-dimethyl-6-((trityloxy)methyl)-4,6a-dihydro-3aH-cyclopenta[d][1,3]dioxol-4-yl)oxy)diphenylsilane (8) with 4,4,5,5-tetramethyl-1,3,2 dioxaborolane.

Embodiments of the process can include preparing tert-butyl(((3aR,4R,6aR)-5-iodo-2,2-dimethyl-6-((trityloxy)methyl)-4,6a-dihydro-3aH-cyclopenta[d][1,3]dioxol-4-yl)oxy)diphenylsilane (8) by reacting (3aS,4R,6aR)-5-iodo-2,2-dimethyl-6-((trityloxy)methyl)-4,6a-dihydro-3aH-cyclopenta[d][1,3]dioxol-4-ol (7) with t-BDPSCl.

Embodiments of the process can include preparing (3aS,4R,6aR)-5-iodo-2,2-dimethyl-6-((trityloxy)methyl)-4,6a-dihydro-3aH-cyclopenta[d][1,3]dioxol-4-ol (7) by reacting (3aR,6aR)-5-iodo-2,2-dimethyl-6-((trityloxy)methyl)-3aH-cyclopenta[d][1,3]dioxol-4(6aH)-one (6) with $CeCl_3$ and $NaBH_4$.

Embodiments of the process can include preparing (3aR, 6aR)-5-iodo-2,2-dimethyl-6-((trityloxy)methyl)-3aH-cyclopenta[d][1,3]dioxol-4(6aH)-one (6) by oxidizing (1R,4S,5S)-2-iodo-4,5-isopropylidenedioxy-1-(trityloxymethyl) cyclopent-2-enol (5). The oxidizing can be with, for example, pyridinium dichromate (PDC).

Embodiments of the process can include preparing (1R, 4S,5S)-2-iodo-4,5-isopropylidenedioxy-1-(trityloxymethyl) cyclopent-2-enol (5) by reacting 1-((4S,5S)-5-(2,2-diiodovinyl)-2,2-dimethyl-1,3-dioxolan-4-yl)-2-(trityloxy)ethanone (4) with n-BuLi.

Embodiments of the process can include preparing 1-((4S, 5S)-5-(2,2-diiodovinyl)-2,2-dimethyl-1,3-dioxolan-4-yl)-2-(trityloxy)ethanone (4) by oxidizing 1-((4R,5S)-5-(2,2-diiodovinyl)-2,2-dimethyl-1,3-dioxolan-4-yl)-2-(trityloxy) ethanol (3). The oxidizing step can be conducted, for example, with pyridinium dichromate (PDC) or by Swern oxidation using diisopropylcarbodiimide, pyridine, trifluoroacetic acid ($CF_3COOH$), and sodium hypochlorite (NaOCl).

Embodiments of the process can include preparing 1-((4R,5S)-5-(2,2-diiodovinyl)-2,2-dimethyl-1,3-dioxolan-4-yl)-2-(trityloxy)ethanol (3) by reacting (3aR,6aR)-2,2-dimethyl-6-((trityloxy)methyl)tetrahydrofuro[3,4-d][1,3]dioxol-4-ol (2) with iodoform.

Embodiments of the process can include preparing (3aR,6aR)-2,2-dimethyl-6-((trityloxy)methyl)tetrahydrofuro[3,4-d][1,3]dioxol-4-ol (2) by reacting (3aR,6aR)-6-(hydroxymethyl)-2,2-dimethyltetrahydrofuro[3,4-d][1,3]dioxol-4-ol (1) with trityl chloride.

Embodiments of the process can include preparing (3aR, 6aR)-2,2-dimethyl-6-((trityloxy)methyl)tetrahydrofuro[3,4-d][1,3]dioxol-4-ol (2) by reacting (3aR,6aR)-6-(hydroxymethyl)-2,2-dimethyltetrahydrofuro[3,4-d][1,3]dioxol-4-ol (1) with trityl chloride.

Embodiments of the process can include preparing (3aR, 6aR)-6-(hydroxymethyl)-2,2-dimethyltetrahydrofuro[3,4-d][1,3]dioxol-4-ol (1), for example by reacting D-ribose with 2,2-dimethoxypropane or by reacting D-ribose with acetone in the presence of acid.

Further objectives and advantages, as well as the structure and function of preferred embodiments will become apparent from a consideration of the description, and non-limiting examples that follow.

DETAILED DESCRIPTION OF THE INVENTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

Nucleosides are known to be the subunits in DNA and RNA macromolecules, and also play roles in neurotransmission (Baldwin, S. A.; Mackey, J. R.; Cass, C. E.; Young, J. D. Mol. Med. Today 1999, 5, 216) and cardiovascular activity (Shryock, J. C.; Belardinelli, L. Am. J. Cardiol. 1997, 79, 2) and as signaling molecules (Schachter, J. B.; Yasuda, R. P.; Wolfe, B. B. Cell Signaling 1995, 7. 659) in addition to their function in cellular biosynthetic pathways.

Nucleosides and their analogues are used for the treatment of cancer, anti-viral infections and AIDS. For example, Gemcitabine (Giessrigl, B. et al. Human Molecular Genetics, 2012, 21(21), 4615-4627; Hertel, L. W.; Kroin, J. S.; Misner, J. W.; Tustin, J. M. J. Org. Chem. 1988, 53, 2406; Plunkett, W.; Huang, P.; Ganghi, V. Nucleosides Nucleotides, 1997, 16, 1261) is approved for the treatment of pancreatic cancer and AZT (3'-Azido-2'3'-dideoxythymidine) is approved for the treatment of HIV (human immunodeficiency virus). Other examples include FMAU (Fluoro-L-arabinofuranosyl)-5-methyluracil, Clevudine) (Wiebe, L. I. et al. Current Radiopharmaceuticals, 2012, 5(1), 38-46; Chu, C. K. et al. Antimicrob. Agents Chemother., 1995, 6, 979) FIAC (Fiacitabine Fluoro L-arabinofuranosyl)-5-iodocytosine) (Prichard, Mark N.; Antiviral Research, 2006, 71(1), 1-6), FLT (Alovudine, 3'-Fluorothymidine) (Agarwal, H. K.; Buckheit, K. W.; Buckheit, R. W.; Parang, K. Bioorganic & Medicinal Chemistry Letters, 2012, 22(17), 5451-5454; Balzarini, J.; Baba, M., Pauwels, R., Herdewijn, P., De Clercq, E. Biochem. Pharmacol. 1988, 37, 2847) F-ddC (2,3-dideoxy-2-fluoro-β-d-threo-pentofuranosyl)-cytosine, 2-fluorodideoxycytidine) (Okabe, M.; Sun, R.-C; Zenchoff, G. B. J. Org. Chem. 1991, 56, 4392) and SFDC (1-(2-Deoxy-2-C-fluoromethylarabinofuranosyl) cytosine) (Yoshimura Y.; Saitoh, K.; Ashida, N.; Sakata S.; Matsuda, A. Bioorganic Med. Chem. Lett., 1994, 4, 721).

Nucleosides can be classified into two major subtypes, N-nucleosides and C-nucleosides, where the bond between the anomeric carbon of the sugar moiety and the base are through the nitrogen or the carbon of the base, respectively. In addition, nucleosides where the sugar ring oxygen is replaced with sulfur, phosphorus, nitrogen and carbon are termed thionucleosides (Yokoyama, M. Synthesis, 2000, 1637), phosphonucleosides (Yamashita, M.; Kato, Y.; Suzuki, K.; Reddy, P. M.; Oshikawa, T. Abstracts of 29th Congress of Heterocyclic Chemistry, 1998, 461), azanucleosides (Yokoyama, M.; Momotake, A. Synthesis, 1999, 1541) and carbocyclic nucleosides (Akella, Lakshmi B.; Vince, Robert From Tetrahedron (1996), 52(25), 8407-8412; Crimmins, M. T. Tetrahedron, 1998, 54, 9229) respectively.

Neplanocin A and (−) Aristeromycin, isolated from natural sources, are members of the carbocyclic nucleosides sub-family. Despite of their potent anti-viral activity only limited structure activity relationship (SAR) studies of these nucleosides has been carried out. The main reason for this shortage is the synthetic difficulty in preparing the D-carbasugars, thus modifications have mainly been done on the base moiety.

Conventional methods of synthesizing carbasugars have the drawback being lengthy routes which do not allow for large scale preparation. For instance: in 2000 Chu's group converted D-glyceraldehyde into E-alkene, an intermediate, in eight (8) steps. The intermediate underwent intramolecular nucleophilic substitution to furnish the fluoro-cyclopentenyl framework (Gumina, G.; Chong, Y.; Choi, Y. Chu, C. K. Org. Lett., 2000, 2, 1229). A similar intermediate was used to give 1,6-diene which underwent ring cyclization metathesis (RCM) using Grubbs' catalyst (Chong, Y.; Gumina, G.; Chu, C. K. Tetrahedron: Asymmetry, 2000, 11, 4853). In 2005 Schmeller and Yin (Yin. X.-Q.; Schneller, S. W. Tetrahedron Lett., 2005, 46, 7535) reported the synthesis of 6'-β-fluoroaristeromycin starting from optically active 4-hydroxy-2-cyclopenten-1-yl acetate in a similar procedure described earlier by Prisbe et al. (Madhavan, G. V. B.; McGee, D. P. C.; Rydzewski, R. M.; Boehme, R.; Martin, J. C.; Prisbe, E. J. Med. Chem., 1988, 31, 1798). These procedures start from a functionalized cyclopentane/cyclopentene skeleton, which is subjected to a sequence of chemical manipulations (e.g., protection strategies, epoxidation, azide formation and fluorination via nucleophilic substitution) to result in the target fluoro-carbocyclic-nucleoside.

Other strategies for fluorocarbocyclic nucleosides from cyclopentene-containing frameworks include Roberts synthesis from a bicyclic ketone system to a 6'-fluorocarbocyclic nucleoside (Payne, A. N.; Roberts, S. M. J. Chem. Soc., Perkin Trans. 1, 1992, 2633), Samuelsson's work starting from enantiomerically pure (3S,4R)-bis(hydroxylmethyl) cyclopentannone ethylene glycol ketal to provide the fluorocarbocyclic moiety in 10 steps (Wachtmeister, J.; Muhlman, A.; Classon, B., Samuelsson B. Tetrahedron 1999, 55, 10761) and Biggadike and Borthwick's route to convert carbocyclic 2'β-fluoro-guanosine derivative into another fluorocarbocyclic nucleoside (Biggadike, K.; Borthwick A. D. J. Chem. Soc., Chem. Commun. 1990, 1380).

In 2008 Schneller's group reported the synthesis of 5'-fluoro-5'-deoxyaristeromycin through Mitsunobu coupling of protected adenine with 4-fluoromethylcyclopentan-1-ol, which was prepared in eleven (11) steps from ribose, and which was transferred into a diene system to enable RCM (Li, W.; Yin, X.; Schneller, S. W. Bioorg. Med. Chem. Lett. 2008, 18, 220).

In 2003 Jeong's group reported the synthesis of fluoroneplanocin A which was found more potent than the parent Neplanocin A (Jeong, L. S. et al. J. Med. Chem., 2003, 46, 201). The key intermediate 3-hydroxymethyl-D-cyclopentenone was prepared from ribose in seven (7) steps involving 2,2-O-isopropylidenetion, Wittig reaction followed by Swern oxidation, Grignard reaction and RCM to form the cyclopentene ring as a mixture of α/β tertiary OH groups. Only the β isomer underwent oxidative rearrangement into the synthon (Choi, W. J. et al. Nucleosides, Nucleotides, and Nucleic Acids, 2005, 24(5-7), 611-613). In 2005 Jeong's group reported the synthesis and the anti-tumor activity of a novel fluorocyclopentenyl-cytosine. The synthesis utilized the latter synthon, which was converted to fluorocyclopentenol in four (4) steps: iodination with I$_2$; stereo and regioselective reduction (of α, β-unsaturated ketone); protection of the resulting OH group with TBDPS (tert-butyldiphenyl-silyl ether); and electrophilic fluorination at the vinyl position via metal halogen exchange, with N-fluorobenzensulfonimide (NFSI) and n-BuLi (Jeong, L. S. et al. Nucleosides, Nucleotides, and Nucleic Acids, 2007, 26, 713-716). The final pyrimidine nucleoside (example 13) was obtained by coupling of protected uracil derivative with the fluorocyclopentenol under Mitsunobu conditions followed by base transformation (Uracil into Cytosine) in three (3) steps (i) POCl$_3$, Et$_3$N; ii) 1,2,4-triazole; iii) NH$_4$OH).

In a method according to the present invention 4-amino-1-((1S,4R,5S)-2-fluoro-4,5-dihydroxy-3-hydroxymethyl-cyclopent-2-enyl)-1H-pyrimidin-2-one (example 13 compound) is synthesized using the reaction scheme 1. Briefly, (3aR,6aR)-6-(hydroxymethyl)-2,2-dimethyltetrahydrofuro[3,4-d][1,3]dioxol-4-ol (1) is prepared by reacting D-ribose with acetone in the presence of acid or by reaction of D-ribose with 2,2-dimethoxypropane, which is tritylated to form (3aR,6aR)-2,2-dimethyl-6-((trityloxy)methyl)tetrahydrofuro[3,4-d][1,3]dioxol-4-ol (2). The tritylate 2 is reacted with iodoform to provide diiodovinyl compound 1-((4R,5S)-5-(2,2-diiodovinyl)-2,2-dimethyl-1,3-dioxolan-4-yl)-2-(tritryloxy)ethanol (3) which is then oxidized by Swern oxidation or using pyridinium dichromate (PDC) to provide 1-((4S,5S)-5-(2,2-diiodovinyl)-2,2-dimethyl-1,3-dioxolan-4-yl)-2-(trityloxy)ethanone (4). Ring closure of 4 is accomplished by the addition of, for example, n-BuLi to provide (1R,4S,5S)-2-Iodo-4,5-isopropylidenedioxy-1-(trityloxymethyl)cyclopent-2-enol (5), which is oxidized to (3aR,6aR)-5-iodo-2,2-dimethyl-6-((trityloxy)methyl)-3aH-cyclopenta[d][1,3]dioxol-4(6aH)-one (6), which can be isolated before reduction to (3aS,4R,6aR)-5-iodo-2,2-dimethyl-6-((trityloxy)methyl)-4,6a-dihydro-3aH-cyclopenta[d][1,3]dioxol-4-ol (7), and protection of the subsequently formed hydroxyl group with, for example, t-BDPSCl (TBDPSCl; tert-butyl-diphenyl chlorosilane) to afford tert-butyl(((3aR,4R,6aR)-5-iodo-2,2-dimethyl-6-((trityloxy)methyl)-4,6a-dihydro-3aH-cyclopenta[d][1,3]dioxol-4-yl)oxy)diphenylsilane (8).

The protected compound 8 can be converted to the fluorinated compound tert-butyl(((3aR,4R,6aR)-5-fluoro-2,2-dimethyl-6-((trityloxy)methyl)-4,6a-dihydro-3 aH-cyclopenta[d][1,3]dioxol-4-yl)oxy)diphenylsilane (9) using a variety of methods. In a first embodiment, conversion is accomplished by reaction with N-fluorobenzensulfonimide (NFSI). Alternatively, protected compound 8 can be converted to a borane intermediate that can be hydrolyzed and fluorinated using of Selectfluor® (1-chloromethyl-4-fluoro-1,4-diazoniabicyclo[2.2.2]octane bis(tetrafluoroborate)). The borane intermediate can be, for example, [(3aR,6S,6aR)-6-[tert-butyl(diphenyl)silyl]oxy-2,2-dimethyl-4-(trityloxymethyl)-6,6a-dihydro-3aH-cyclopenta[d][1,3]dioxol-5-yl]boronic acid (9c-1), prepared by reacting the protected compound 8 with trimethylborate, or [(3aR,6S,6aR)-2,2-dimethyl-5-(4,4,5,5-tetramethyl-1,3,2-dioxaborolan-2-yl)-4-(trityloxymethyl)-6,6a-dihydro-3aH-cyclopenta[d][1,3]dioxol-6-yl]oxy-tert-butyl-diphenyl-silane (9c-2), prepared by reacting the protected compound 8 with 4,4,5,5-tetramethyl-1,3,2 dioxaborolane.

The fluorinated compound 9 is deprotected to (3aS,4R,6aR)-5-fluoro-2,2-dimethyl-6-((trityloxy)methyl)-4,6a-dihydro-3aH-cyclopenta[d][1,3]dioxol-4-ol (10), for example by reaction with tetra-n-butylammonium fluoride (TBAF), and mesylated to give (3aR,4R,6aR)-5-fluoro-2,2-dimethyl-6-((trityloxy)methyl)-4,6a-dihydro-3aH-cyclopenta[d][1,3]dioxol-4-yl methanesulfonate (11). The mesylate 11 is reacted with cytosine to give 4-amino-1-(3 aS,4S,6aR)-5-fluoro-2,2-dimethyl-6-((trityloxy)methyl)-4,6a-dihydro-3 aH-cyclopenta[d][1,3]dioxol-4-yl)pyrimidin-2(1H)-one (12) which is fully deprotected to provide 4-amino-1-((1 S,4R,5S)-2-fluoro-4,5-dihydroxy-3-(hydroxymethyl)-cyclopent-2-en-1-yl)-pyrimidin-2(1H)-one (13).

The reactions in scheme 1 can be accomplished utilizing the reaction conditions described in more detail herein and as shown in the examples. However, the examples are intended to be illustrative and not limiting. Persons of ordinary skill in the art will recognize other methods to accomplish the reactions and conversions described herein and will recognize certain equivalents, for example use of alternative protecting groups, may be substituted for the specific reagents, protecting groups, etc. described herein.

Scheme 1

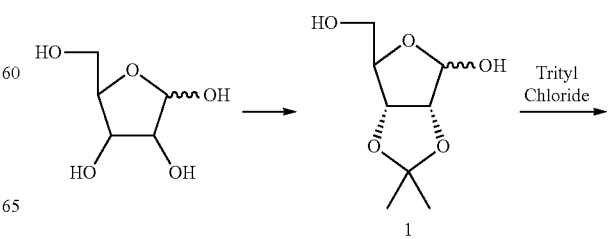

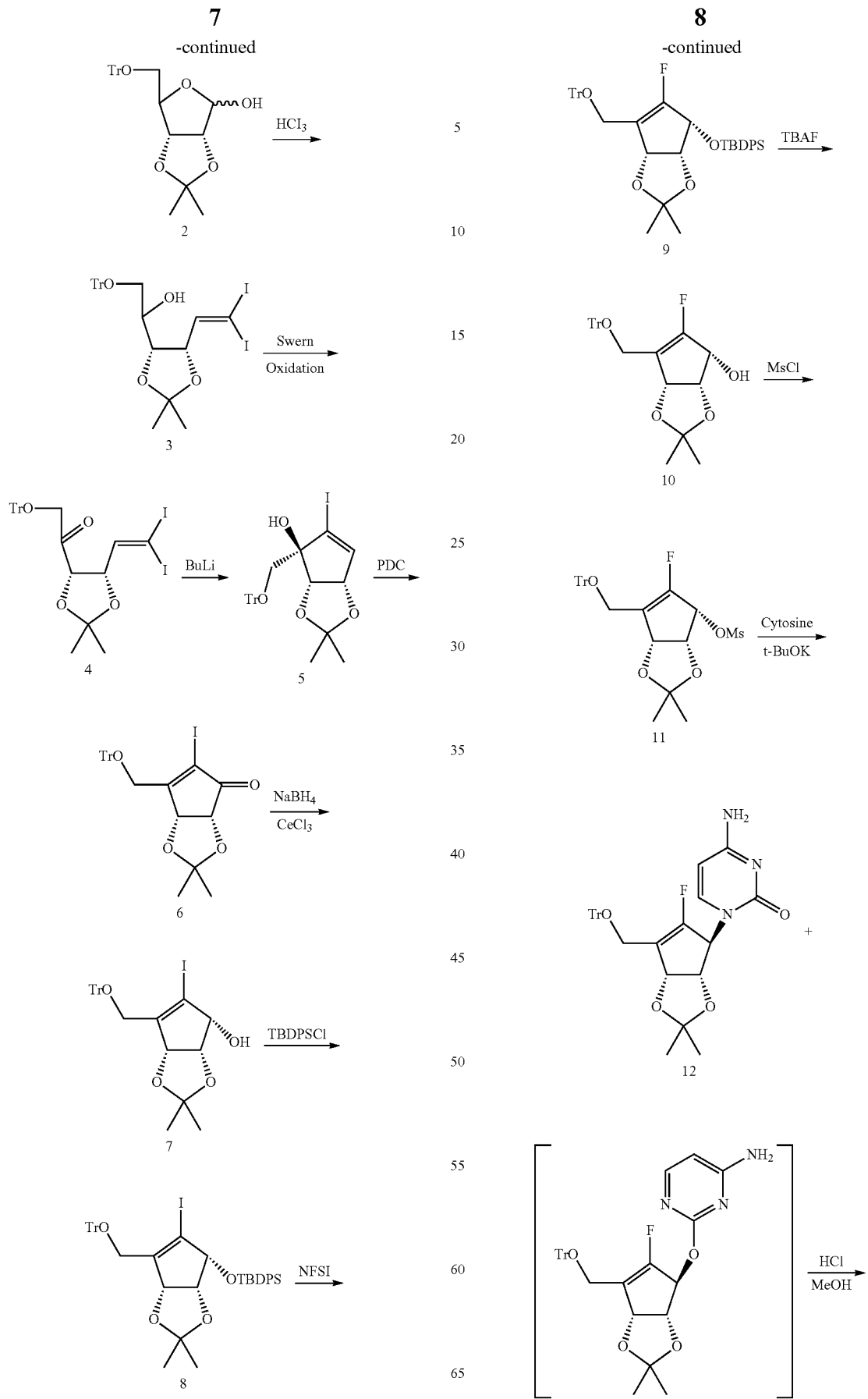

-continued

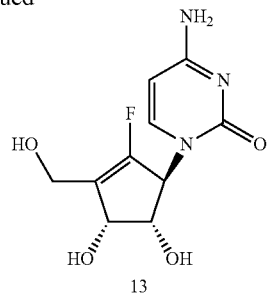

13

This method does not require the use of expensive Grubbs's catalyst (a transition metal (e.g., ruthenium) carbene complex), to effect ring-closure-metathesis (RCM) in construction of the carbasugar (C-carbohydrate ring, that is, the ring O is replaced by C). Furthermore, this method does not require a Grignard reaction to introduce a vinyl moiety to form the diene system to enable the RCM. During this latter step, the exothermic Grignard reaction at scale presents substantial safety issues. Furthermore, Grignard reactions are difficult to initiate and it is difficult to detect when initiation has occurred. This can result in variation from batch to batch, and, if initiation is delayed, there might be an effect on the impurity profile. The heterogeneous Grignard reaction might result in mixing issues in a scaled-up process. The alternative ring closure method set forth in Scheme 1 is safer when scaled up, more time and cost effective, does not require heating, does not require a long duration of reaction, and does not require expensive $2^{nd}$ generation Grubbs' catalyst. As such, the synthesis set forth in Scheme 1, above, has advantages over other synthetic schemes in the art.

In Scheme 1, iodoform is reacted with compound 2 under Wittig conditions to give compound 3 which is oxidized into 4, so that no separate iodination step is required. Compound 4 can undergo intramolecular ring closure and entry into the cyclopentenol 5. The synthesis of Scheme 1 is shorter than other synthetic schemes in the art. Scheme 1 is scalable for plant manufacturing and adaptable to manufacturing of compound 9 in kilogram scale, as set forth in the examples below. The present inventive route avoids the use of potentially hazardous POCl$_3$ and NH$_4$OH. To our knowledge, there is no previous example in the scientific and patent literature of a direct coupling of cytosine with a carbasugar derivative.

Several different N$^4$-acylated cytosines were prepared: acetyl, trifluoroacetyl, benzoyl, 4-methoxy benzoyl and BOC, as well as the silylated derivatives bistrimethylsilyl cytosine and bistrimethylacetyl cytosine. These were reacted with various derivatives of the alcohol of compound 10 (such as the mesylate). A nearly 1:1 mixture of N$^1$-alkylated/O-alkylated cytosine was obtained.

The reaction schemes set forth herein include a direct transformation with desired region-selectivity to form, for example, the compound 13 (4-amino-1-((1S,R4,5S)-2-fluoro-4,5-dihydroxy-3-(hydroxymethyl)cyclopent-2-en-1-yl)pyrimidin-2(1H)-one), including a novel entry into carbasugars.

A reaction using the mesylate 11 and displacement with cytosine under KO$^t$Bu/DMSO conditions gave complete conversion, approximately 90% in favour of the desired N$^1$-alkylated product, with the remainder being the O-alkylated product. The two were readily separated by chromatography. After subsequent trityl and acetonide deprotection, compound 13 was afforded with chemical purity of 98.34% area in 50% yield from alcohol 10.

The synthetic process according to the present invention has advantages over syntheses in the prior art, for example in terms of shorter route, avoidance of expensive catalyst, ability to be adapted for bulk production and avoidance of the separations using silica gel column chromatographic techniques.

EXAMPLES

The following Examples, exemplify some of the embodiments according to the present invention. The following Examples are not to be considered to limit the invention in any way.

For example, a person skilled in the art will understand that in certain instances polar (e.g., water, dimethylsulfoxide, dimethylformamide, and methanol), apolar (e.g., hexane, ethyl acetate, tetrahydrofuran, and dichloromethane), protic (e.g., water, methanol, and ethanol), aprotic (e.g., tetrahydrofuran, ethyl acetate, dimethylformamide, and dimethylsulfoxide), electron—pair donor (e.g., tetrahydrofuran and methanol), and non-electron-pair donor solvents other than those set forth in the process steps below can be used. For example, a person skilled in the art will understand that in certain instances the ionic strength of a solution may be varied from what is set forth in the process steps below can be used. For example, in certain instances, a salt or salts different than those set forth in the process steps below can be used to induce precipitation of a compound or compounds. In certain instances, a precipitation step can be skipped or eliminated, in other instances, a precipitation step can be added. In certain instances, a single solvent may be substituted for a mixture of solvents; in other instances, a mixture of solvents may be substituted for a single solvent. For example, a person skilled in the art will understand that in certain instances temperatures other than those set forth in the syntheses below can be used; for example, temperatures that are 1, 2, 5, 10, 15, 20, 25, or 30° C. greater or lesser than the temperatures set forth can be used in certain instances. For example, "ambient temperature" can mean about 5, 10, 15, 20, 22, 25, 30, 35, 40, or 45° C. For example, "room temperature" can mean about 5, 10, 15, 20, 22, 25, 30, 35, 40, or 45° C. For example, a person skilled in the art will understand that in certain instances pH values other than those set forth in the syntheses below can be used; for example, a pH that is 0.1, 0.2, 0.5, 1, 2, 3, 4, or 5 pH units greater or lesser than the pH value set forth can be used in certain instances. For example, a person skilled in the art will understand that in certain instances times for reaction, stirring, dissolution, or other process steps other than those set forth in the syntheses below can be used; for example, times that are 25%, 33%, 50%, 67%, 80%, 125%, 150%, 200%, 300%, or 400% of those set forth can be used in certain instances. For example, a person skilled in the art will understand that in certain instances the proportion of a reactant to another reactant and/or the ratio of a reactant to solvent other than those set forth in the syntheses below can be used. For example, in certain instances the weight percentage of one or more reactants, solvents, precipitation agents, or other materials or compounds in a mixture may be 25%, 33%, 50%, 67%, 80%, 125%, 150%, 200%, 300%, or 400% of those set forth in the below examples. For example, a person skilled in the art will understand that in certain instances a reactant other than indicated in the syntheses below can be used. For example, a person skilled in the art will understand that in certain instances a reactant and/or a solvent of greater or lesser purity than indicated in the syntheses below can be used. For example, a person skilled in the art will understand that in certain instances a process step, such as a purification, separation, or extraction step may be modified from those set forth below or that a different process step may be substituted. For example, a person of skill in the art will understand that a drying agent or agents different than that or those specified can be substituted, and or that a nearly complete (high), partial, or no vacuum can be substituted for a pressure condition specified in certain instances. For example, a person skilled in the art will understand that in certain instances molecular sieves other than those set forth below may be used. For example, in certain instances, activated carbon, silica gels, clays, glasses, and zeolites may be substituted for each other. For example, a person skilled in the art will understand that in certain instances separation techniques and/or chromatographic techniques other than those set forth below may be used. For example, a person skilled in the art will understand that in certain instances chromatographic media and/or substrates other than those set forth below may be used. For example, a person skilled in the art will understand that in certain instances a process step, such as a synthetic and/or purification step, may be split into two or more separate process steps, and that in other instances two or more separate process steps may be combined into a single process step. For example, a person skilled in the art will understand that in certain instances a process step, such as a purification step, may be skipped or eliminated, and that in other instances a process step, such as a purification step, may be added. For example, a person skilled in the art will understand that in certain instances process steps, such as synthetic and/or purification steps, can be performed in a different order than set forth below. For example, a person skilled in the art will understand that in certain instances a different analytical technique than those set forth below or an analytical technique run under different conditions than those set forth below can be used. In certain instances, an analytical step set forth below (for example, to determine the amount or concentration of a product component) can be skipped, in other instances an analytical step can be added. A person skilled in the art will understand that such modifications to reactants used, solvents used, reaction conditions, such as temperature, time, and concentrations and relative proportions of reactants and/or solvents, synthetic steps, purification, separation, and/or extraction steps and techniques, materials used in separation and/or purification steps, and analytical techniques can be made to further optimize process parameters such as yield and purity and overall process economics (such as overall time and number of steps and cost of materials, such as reactants and solvents, used), and that such modifications are within the scope of the present invention and embodiments of the invention set forth herein.

The reactions disclosed herein are demonstrated for specific compounds. However, these reactions can apply to other structurally related compounds. Persons skilled in the art will recognize that the reactions can be used on structurally similar compounds, for example, when used in the field of carbasugars.

General

All chemicals were reagent grade and were purchased from Aldrich Chemical Company (Milwaukee, Wis.) or Sigma Chemical Company (St. Louis, Mo.). Solvents were routinely distilled prior to use. Anhydrous tetrahydrofuran was distilled from sodium/benzophenone prior to use.

Proton NMR spectra were recorded on a Varian-400 MHz spectrometer in deuterated solvents such as DMSO-$d_6$, CDCl$_3$, acetonitrile-$d_3$ or acetone-$d_6$. Chemical shifts are reported in parts per million (ppm) with tetramethylsilane (TMS) as an internal standard at zero ppm. Coupling constants (J) are given in hertz (Hz) and the abbreviations s, d, t, q, and m refer to singlet, doublet, triplet, quartet and multiplet, respectively. TLC was performed on Merck precoated 60F$_{254}$ plates. Column chromatography was performed using silica gel 60 (230-400 mesh, Merck).

Example 1

Example 1a (3aR,6aR)-6-(hydroxymethyl)-2,2-dimethyltetrahydrofuro[3,4-d][1,3]dioxol-4-ol (1)

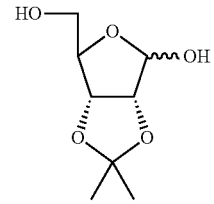

Into a 2000 L reactor was charged acetone (1200 L) and 2,2-dimethoxypropane (125 kg, 1200 mol, 1.2 eq), followed by D-ribose (150 kg, 999 mol). The mixture was stirred at ambient temperature. p-TSA (p-toluene sulfonic acid) (9.6 kg, 49.5 mol, 0.05 eq) was added in portions over 40 minutes. The reaction mixture was heated at 30° C. and monitored by TLC every hour. After 14 hours, TLC indicated complete conversion. A sample from the reaction mixture and standard samples for ribose and ribose acetonide were applied to a commercial silica gel TLC plate, and the plate was run in the mobile phase dichloromethane/ethanol=8:1. The plate was then sprayed with 10% H$_2$SO$_4$ in ethanol and heated using a heat gun. Ribose-related compounds gave dark spots on the plate. The R$_f$ for Ribose was ~0.1, while R$_f$ for ribose acetonide (1) was usually 0.3-0.35. To the reaction mixture was added triethylamine (8.1 kg, 0.08 eq). Acetone was distilled under vacuum (water bath temperature <60° C.) over 12 hours. The residue was diluted with dichloromethane (300 L). The mixture was stirred for 0.5 hour at ambient temperature, and then solvent was removed under vacuum over 4 hours. This operation was repeated once, and the residue was used in next step without further purification. $^1$H NMR (400 MHz, CD$_3$OD) δ 1.31 (s, 3H, CH$_3$), 1.44 (s, 3H, CH$_3$), 3.59 (dd, J=5.6, 12.0 Hz, 1H, HOCHH), 3.63 (dd, J=4.8, 12.0 Hz, 1H, HOCHH), 4.19 (irregular t, J=4.4, 5.2 Hz, 1H, 4-H), 4.52 (d, J=6.0 Hz, 1H, 3-H), 4.77 (d, J=6.0 Hz, 1H, 2-H), 5.26 (s, 1H, anomeric H). Anal. calcd for C$_8$H$_{14}$O$_5$: C, 50.52; H, 7.42. Found: C, 50.48; H, 7.36; $[\alpha]^{25}_D$ −36.2 (c 1.45, acetone) [lit., $[\alpha]^{25}_D$ −37 (c 0.53, acetone)].

Example 1b

To the 1000 L reactor 1 was charged 312 kg acetone and 40.0 kg D-Ribose, and the reaction mixture was cooled to 5-10° C. 1.60 kg of concentrated H$_2$SO$_4$ was added drop wise at 5-10° C. and the mixture was stirred at 5-10° C. for 1 hour after which time the mixture was allowed to warm to 25-30° C. and stirred for an additional 2 hrs. HPLC (ELSD) showed that 3.5% of D-ribose remained. The reaction mixture was cooled to <-5° C. and slowly added into a mixture of 160 kg of acetone, 8.5 kg Na$_2$CO$_3$, 20 kg Na$_2$SO$_4$ in 1000 L reactor 2 and the mixture was stirred at 5±5° C. for 1 h to result in neutralization (pH>7). The mixture was filtered to remove Na$_2$SO$_4$, extra Na$_2$CO$_3$ and salt, and the cake was washed with acetone (10 kg×3). The combined acetone solution (504 kg, of which 702 g sampled was concentrated to 74.2 g residue to estimate 53.3 kg of total crude 1) was concentrated under vacuum at <20° C. followed by addition of 120 kg DCM (dichloromethane) and removal of the solvent at 20-25° C. under vacuum to furnish crude 1 (KF, 0.4%) to which 692 kg DCM were added. The solution was used directly in the next stage.

Example 2a (3aR,6aR)-2,2-dimethyl-6-((trityloxy)methyl)tetrahydrofuro[3,4-d][1,3]dioxol-4-ol (2)

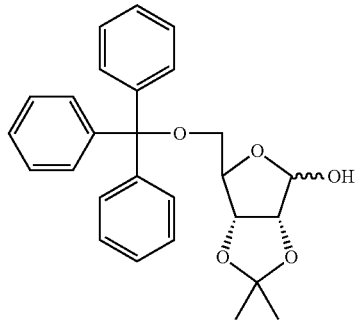 [SMILES: CC1(C)O[C@@H]2C(COC(c3ccccc3)(c3ccccc3)c3ccccc3)OC(O)[C@@H]2O1]

To the residue from the last step (Example 1a) (~189 kg, 999 mol) in the 2000 L (Example 1a) reactor was charged 900 L of DMF (dimethylformamide), and the solution was stirred 0.5 hour at ambient temperature. To the stirred solution was added trityl chloride (Trt-Cl, 336 kg, 1200 mol, 1.2 eq), triethylamine (202 kg, 1998 mol, 2 eq) and DMAP (dimethylaminopyridine) (7.3 kg, 60 mol, 0.06 eq). The mixture was stirred 32 hours at 30° C. TLC showed complete conversion (sample from the reaction mixture and standard samples for compounds 1 and 2 were applied to a commercial silica gel TLC plate, and the plate was run in the mobile phase petroleum ether/ethyl acetate=4:1. Compound 2, trityl chloride, trityl alcohol and trityl methyl ether can be detected under UV$_{254}$. They can also be visualized using iodine treatment. The R$_f$ for trityl methyl ether was ~0.9. The R$_f$ for compound 2 was ~0.4. The R$_f$ for trityl alcohol was ~0.3. Compound 1 does not move on TLC plate using this method. It can be detected using the TLC method described for Example 1a. Methanol (50 L) was added in one portion, the reaction was stirred for another 1 hour. Half of this material was transferred to another 2000 L reactor. The reaction mixture in each reactor was diluted with aqueous saturated ammonium chloride (600 L) over 0.5 hour with stirring, then with ethyl acetate (500 L). The layers were cut. The aqueous layer in each reactor was extracted with 150 L of ethyl acetate. The combined ethyl acetate extract (about 1400 L) was introduced into a 2000 L reactor, washed twice with brine (300 L) and dried 6 hours over sodium sulfate. Ethyl acetate was distilled under vacuum over 15 hours (water bath temperature <60° C.) to about 600 L volume. This residue was used in the following chromatography. The residue from above was divided into 20 portions. Each portion was added to 30 kg of silica gel (100-200 mesh) in a 100 L container with vigorous stirring to get an even mixture. The silica gel with crude product was then dried in a vacuum oven over 12 hours. To a column (1500 mm, φ 400 mm) was added 4 kg of silica gel (200-300 mesh). On the top was added 2.5 kg of silica gel with crude product. Fifteen such columns were run at the same time and monitored by TLC. The column was first washed with petroleum ether/ethyl acetate/dichloromethane=10:1:1 (60 L), then changed to petroleum ether/ethyl acetate/dichloromethane=5:1:1. These fifteen columns usually took three to five hours to complete. The eluates were monitored by TLC. Eluates with compound 2 as major component were combined. The combined eluate was concentrated in a 300 L reactor to ~50 L under vacuum (water bath not exceeding 60° C.). The set of the fifteen columns was carried out 34 times for this batch. The concentrated eluates were combined and further concentrated to about 200 L under vacuum in a 500 L reactor (water batch not exceeding 60° C.). To the residue was added 100 L of toluene, and the mixture was distilled under vacuum to near dryness to remove residue water (water bath at 60° C.). Another 100 L of toluene was added, and the distillation was repeated. Altogether 115 kg of compound 2 was obtained. $^1$H-NMR (300 MHz, CDCl$_3$), δ 7.21-7.40 (m, 15H), 5.72 (d, J=4.0 Hz, 0.4H), 5.32 (s, 0.6H), 4.76 (d, J=5.6 Hz, 0.6H), 4.72 (dd, J=6.0, 4.0 Hz, 0.4H), 4.63 (d, J=6.0 Hz, 0.6H), 4.57 (dd, J=6.4, 1.2 Hz, 0.4H), 4.33 (m, 0.6H), 4.17 (m, 0.4H), 4.09 (bs, 2H), 3.40 (dd, J=10.4, 2.8 Hz, 0.4H), 3.39 (dd, J=10.0, 3.6 Hz, 0.6H), 3.32 (dd, J=10.0, 3.6 Hz, 0.6H), 3.00 (dd, J=10.4, 3.2 Hz, 0.4H), 1.53 (s, 1.2H), 1.46 (s, 1.8H), 1.35 (s, 1.2H), 1.32 (s, 1.8H).

Example 2b

To compound 1 (almost 120 kg) and 1590 kg DCM was added 152 kg of trityl chloride at -5 to -10° C. under nitrogen atm. in a 2000 L reactor and a solution of TEA (triethylamine) (71 kg) and DMAP (2.88 kg) in DCM 175 kg was slowly added. The reaction mixture was stirred at -5 to -10° C. for 32 hr and warmed to 15-20° C. (4° C./h) and kept at 15-20° C. for 12 h after which time LC-MS showed trityl chloride <2%. The reaction was quenched by 20 kg water, the organic phase was separated, dried and concentrated to a residue, and MTBE (methyl tert-butyl ether) (500 kg) was added, with stirring to result in a clear solution. Water (600 kg) was added, and the mixture was stirred for 3 h, then 500 kg heptane was added, cooled to -5° C.-0° C. and stirred for 3 h. A small amount of yellow solid precipitated, filtered by a centrifuge. Then the organic layer washed with saturated NH$_4$Cl solution (600 kg), pH was adjusted with 0.5 N aqueous citric acid to pH=3-4, and the organic layer collected, dried with Na$_2$SO$_4$, filtered and concentrated under vacuum to get crude compound (2), (3aR,6aR)-2,2-dimethyl-6-((trityloxy)methyl)tetrahydrofuro[3,4-d][1,3]dioxol-4-ol, as oil. This crude (2) (228.5 kg) was purified by silica gel column (1.0× of silica gel was used to pre-absorb the crude material, 2.3× of silica gel was used to pack the column), eluted by the solvent (EA(ethyl acetate): PE(petroleum ether)=1:8), to get 93 kg (four batches) of (2) dispersed in toluene (assay by HPLC).

Example 3a 1-((4R,5S)-5-(2,2-diiodovinyl)-2,2-dimethyl-1,3-dioxolan-4-yl)-2-(trityloxy)ethanol (3)

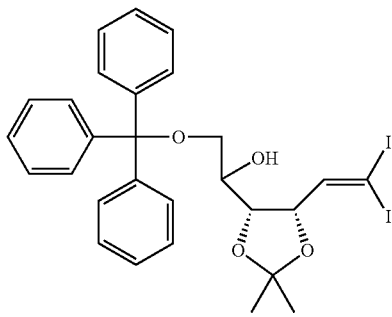 [SMILES: CC1(C)O[C@@H](C=C(I)I)[C@@H](C(O)COC(c2ccccc2)(c2ccccc2)c2ccccc2)O1]

Into a 20 L reactor was charged triphenylphosphine (2.55 kg, 9.72 mol, 2.1 eq) and iodoform (3.83 kg, 9.72 mol, 2.1 eq), followed by toluene (8 L). The stirred solution was cooled down to −20° C. in dry ice/acetone bath. Potassium tert-butoxide (1.13 kg, 9.26 mol, 2 eq) was added in portions (within ~30 minutes) while keeping reaction temperature <10° C. The mixture turned dark and some precipitates formed. After addition, the suspension was stirred another hour at 5-10° C. A solution of compound 2 (2 kg, 4.63 mol, 1 eq) in toluene (5 L) was added to the suspension at 5° C. The reaction was quenched with brine (1.5 L) after 1.5 hours. HPLC showed the ratio of 2 (6.4 min) and 3 (~9.8 min) as about 1:3, while little or no by-product 3a (where the OH group of 3 is added with elimination of HI onto the double bond of 2 to form (3aR,6aR)-4-(iodomethylene)-2,2-dimethyl-6-((trityloxy)methyl) tetrahydrofuro[3,4-d][1,3]dioxole) was observed. The reaction mixture was diluted with ethyl acetate (2 L) and stirred 15 minutes to get a diluted suspension. Eight such 20 L reactions were combined. The supernatant was decanted and centrifuged. The residue was diluted with water (40 L) and ethyl acetate (40 L). The suspension was stirred for 10 minutes and then centrifuged. The solid was washed with 40 L of ethyl acetate once. The filtrate and wash were combined. Layers were cut. The organic layer was washed with brine (30 L) and water (30 L). It was then concentrated to dryness (temperature of the water bath <50° C.). The residue was loaded on a silica column and eluted first with petroleum ether/ethyl acetate (10:1), and then with petroleum ether/ethyl acetate/dichloromethane (20:1:1). After the desired product appeared, the column was washed with petroleum ether/ethyl acetate/dichloromethane (5:1:1). Altogether 5.3 kg of 3 was obtained (HPLC purity 95%, yield 21%). A sample from the reaction mixture and standard samples for compounds 2 and 3 were applied to a commercial silica gel TLC plate, and the plate was run in petroleum ether/ethyl acetate=4:1. Compounds 2, 3 and 3a can be detected under $UV_{254}$. They can also be visualized with iodine. The $R_f$ for compound 2 was ~0.4. The $R_f$ for 3 was ~0.7. The $R_f$ for 3a was ~0.9; $^1$H-NMR (300 MHz, CDCl$_3$), δ 7.23-7.46 (m, 15H), 7.05 (d, J=8.4 Hz, 1H), 4.53 (dd, J=5.7, 8.4 Hz, 1H), 4.19 (dd, J=5.7, 8.4 Hz, 1H), 3.67 (m, 1H), 3.32 (d, J=4.8 Hz, 2.46 (d, J=4.8 Hz, 1H), 1.34 (s, 3H), 1.33 (s, 3H); $^{13}$C-NMR (75 MHz, CDCl$_3$) δ 147.65 (—CH═CI$_2$), 143.75, 128.68, 128.00, 127.29, 127.23, 109.55, 86.97, 83.39, 77.21, 69.19, 27.84, 25.52, 15.99 (═CI$_2$).

Example 3b

To a 1000 L flask was added toluene (344 kg) and THF (110 kg) under N$_2$ flushing. Iodoform (58.4 kg) was added and stirred at room temperature for 10 min to give a homogeneous solution to which molecular sieves (50 kg) were added, and the mixture was stirred for 13 h (water content was 110 ppm by KF), after which molecular sieves were filtered and PPh$_3$ (37.2 kg) was added and the mixture was stirred at 10° C. for 30 min and cooled to 0-5° C. Then t-BuOK (15.6 kg) was added in a few portions, during which the temperature was kept as <15° C. resulting in a suspension which was stirred at 25° C. for 10 h. 2 (28 kg) solution in 80 kg toluene (KF: no water was detected) was added drop wise into the Wittig mixture and the mixture stirred for 3 h at 10° C. IPC (in process control) by HPLC showed ~5.5% 2 was left). 2.0 kg water was added to quench the reaction and after 30 min, Na$_2$SO$_4$ (50 kg) was added and stirred for 3 h. Then the solid was filtered, cake was slurried with 100 kg toluene and the solid filtered. The organic layers were combined (HPLC assay showed about 23.07 kg 3 in the organic layer), dried and cooled to 0-10° C. and the solution was used in the next oxidation step without further purification.

Example 4a 1-((4S,5S)-5-(2,2-diiodovinyl)-2,2-dimethyl-1,3-dioxolan-4-yl)-2-(trityloxy)ethanone (4)

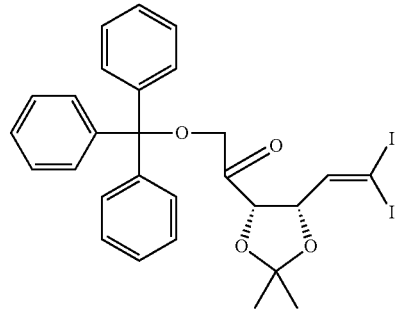 [SMILES: CC1(C)O[C@@H](C=C(I)I)[C@@H](C(=O)COC(c2ccccc2)(c2ccccc2)c2ccccc2)O1]

Compound 3 (38 kg, 55.7 mol) was dissolved in 100 L of dichloromethane and the solution was added into a 1000 L reactor charged with dichloromethane (500 L) followed by addition of 4 Å molecular sieves (42.9 kg) and neutral alumina (84 kg). To the stirred suspension at ambient temperature was added PDC (pyridinium dichromate) (25.1 kg, 66.8 mol) and the mixture was stirred 16 hours, until HPLC indicated complete conversion. The suspension was filtered using a centrifuge. The filtrate from the centrifuge was collected. The cake from the centrifuge (mainly alumina, molecular sieves and PDC residue) was washed with 2×100 L of methyl tert-butyl ether. The combined filtrate and wash was introduced into a 1000 L reactor and concentrated to dryness while keeping the heating below 50° C. To the residue was added 600 L of methyl tert-butyl ether, followed by 5 kg of activated carbon. The dark suspension was heated 1 hour at 60° C., then cooled down to 30° C. It was filtered through a pad of Celite to remove activated carbon. The filtrate was concentrated to dryness. The oily residue was diluted with 60 L of methanol and precipitates started to form. The thick suspension was stirred 1 hour at ambient temperature, then the precipitates were collected by filtration. The cake was washed twice with 50 L of petroleum ether and dried at 40° C. to afford 25.3 kg of 4 (yield 67%, purity >99%) as white solid. The $R_f$ for 3 was ~0.7, while $R_f$ for 4 was ~0.75 on silica gel TLC plate run in petroleum ether/ethyl acetate=4:1 and visualized under $UV_{254}$ light or by using iodine treatment. $^1$H-NMR-(300 MHz, $CDCl_3$) δ 7.23-7.48 (m, 15H), 6.80 (d, J=7.5 Hz, 1H), 4.75-4.85 (m, 2H), 3.95 (d, J=18.0 Hz, 1H), 3.80 (d, J=18.0 Hz, 1H), 1.41 (s, 3H), 1.34 (s, 3H); $^{13}$C-NMR (75 MHz, $CDCl_3$) δ 203.22, 145.93 (—CH=$Cl_2$), 143.07, 128.62, 128.52, 128.21, 128.08, 127.43, 111.01, 87.57, 82.95, 80.00, 69.10, 26.85, 25.11, 18.53 (=$Cl_2$).

Example 4b

To the final solution in Example 3b was added DMSO (dimethyl sulfoxide) (5.2 kg), DIC (diisopropylcarbodiimide) (7.9 kg) and pyridine (7.6 kg). Then $CF_3COOH$ (4.9 kg) was added drop-wise, keeping the temperature <20° C. (exothermic reaction) and the mixture was stirred for an hour. Then additional DMSO (2.6 kg), DIC (3.9 kg) and pyridine (3.8 kg) were added followed by drop-wise addition of $CF_3COOH$ (2.45 kg) at <20° C. HPLC showed full consumption of 3. The reaction mixture was cooled to 0-5° C. NaOCl (~7%, 108 kg,) was added slowly with stirring for 1 h after which the mixture was filtered, the solid was washed (2×30 kg of toluene), the layers were separated and the organic phase was washed with water (2×200 kg), brine (250 kg) and distilled under reduced pressure <65° C. to a residue. The residue was cooled to 0-5° C., ethanol was added (120 kg) and the solution was stirred at 0° C. for 4 h resulting in a slurry. The solid was filtered and dried to give pure 4 (19.2 kg).

The formation of 4 from 3 can be carried out with Moffat oxidation or Swern oxidation.

Example 5a (1R,4S,5S)-2-Iodo-4,5-isopropylidenedioxy-1-(trityloxymethyl)cyclopent-2-enol (5)

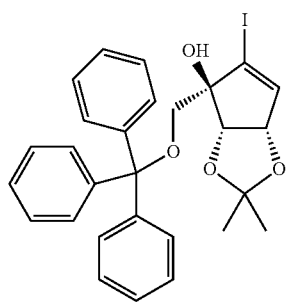 [SMILES: CC1(C)O[C@H]2C=C(I)[C@@](O)(COC(c3ccccc3)(c3ccccc3)c3ccccc3)[C@H]2O1]

Into a 20 L reactor was added 4 (1.5 kg, 2.2 mol) and anhydrous THF (7 L). The stirred solution was cooled down to <−70° C. n-BuLi (2.5 M, 1.06 L, 2.65 mol, 1.2 eq) was added drop wise to the reaction mixture at such a rate that temperature did not exceed −65° C. It took about 1.5 hour. The reaction mixture was stirred 1 hour at below −70° C. HPLC indicated complete consumption of 4. A saturated solution of ammonium chloride (1 L) was added drop wise to the reaction mixture. The mixture was then allowed to warm up to room temperature. Eight such 20 L reactions were combined and introduced into a 300 L reactor. The mixture was partitioned between brine (16 L) and ethyl acetate (60 L) and stirred for 30 minutes. The layers were cut. The organic layer was washed with brine (20 L), dried over sodium sulfate, and concentrated under vacuum (temperature <40° C.). The residue was put on a silica gel column. The column was eluted with petroleum ether/ethyl acetate/dichloromethane=15:1:1. Altogether 4.09 kg of 5 were obtained (yield 42%, HPLC >95%). Sample from the reaction mixture and standard samples for compounds 4 ($R_f$~0.75) and 5 ($R_f$~0.55) were run on silica gel TLC plate in petroleum ether/ethyl acetate=4:1 visualizing with $UV_{254}$ light and also by iodine treatment. $^1$H-NMR (300 MHz, $CDCl_3$) δ 7.31-7.62 (m, 15H), 6.50 (d, J=1.8 Hz, 1H), 5.24 (dd, J=1.8 Hz, 5.7 Hz, 1H), 4.68 (d, J=5.7 Hz, 1H), 3.69 (d, J=9.0 Hz, 1H), 3.36 (s, 1H, OH), 3.27 (d, J=9.0 Hz, 1H), 1.46 (s, 3H), 1.36 (s, 3H); $^{13}$C-NMR (75 MHz, $CDCl_3$) δ 144.23 (—CH=Cl—), 143.53, 128.89, 127.95, 127.29, 112.44, 104.99 (=Cl—), 87.64, 85.66, 84.40, 83.10, 65.40, 27.45, 26.62.

Example 5b

Compound 4 (29.0 kg) was dissolved in THF (220.0 kg, 247 L, KF: 190 ppm) and cooled to −75° C. n-BuLi (17.8 kg, 1.15 eq) was added at temperature below −70° C. over 3 hrs., then the mixture was stirred at −70±2° C. for 3 hrs. after which time HPLC indicated almost complete consumption of 4 (5.9% area remained) and formation of 5. Therefore, the reaction mixture warmed slowly to −40° C. over 1.5 hrs followed by slow and continuous warming of the reaction mixture to −25° C. over 1.5 hrs to result in only 1.1% of 4. The reaction was added to saturated $NH_4Cl$ (15 kg) in 1 h, the mixture was kept at −7±2° C. while quenching. Then the mixture was extracted with EA (4.5 kg×2). The EA phase (23 kg) was dried over $Na_2SO_4$ then concentrated in vacuum at 40° C. in −0.08 MPa for about 5 hrs. The residue was dissolved in DCM (10.1 kg) to afford solution of 5 (10.7 kg) which was used in the next oxidation step.

This reaction from 4 to 5 is a general reaction, which is, for example, useful for forming carbocyclic compounds. This reaction has not previously been reported. For example, this reaction can be used with other reactants and products.

Example 6a (3aR,6aR)-5-iodo-2,2-dimethyl-6-((trityloxy)methyl)-3aH-cyclopenta[d][1,3]dioxol-4(6aH)-one (6)

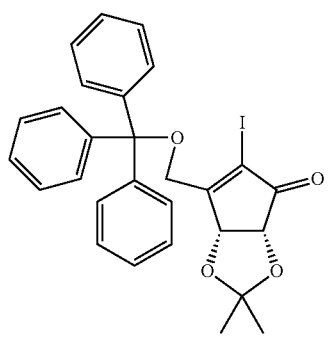 [SMILES: CC1(C)O[C@@H]2C(COC(c3ccccc3)(c3ccccc3)c3ccccc3)=C(I)C(=O)[C@@H]2O1]

Into a 100 L reactor was added a solution of 5 (5.54 kg, 10 mol) in dichloromethane (50 L), followed by 4 Å molecular sieves (8.3 kg) and neutral alumina (16.6 kg) and PDC (12.03 kg, 32 mol). The suspension was stirred for 12 hours at ambient temperature. HPLC indicated complete conversion. The suspension was centrifuged. The cake was washed with methyl tert-butyl ether (2×50 L). The combined filtrate and wash was introduced into a 200 L reactor and concentrated under vacuum to dryness (heating temperature kept <50° C.). To the residue was added 100 L of methyl tert-butyl ether, followed by 0.5 kg of activated carbon. The dark suspension was heated for 1 hour at 60° C. and then cooled down to 30° C. and then filtered through a pad of Celite. The filtrate was concentrated to dryness. The residue was diluted with 6 L of methanol. The thick suspension was stirred 2 hours at ambient temperature and then filtered. The cake was washed twice with 5 L of petroleum ether, and dried in a vacuum oven (<40° C.) to afford 2.94 kg of 6 (yield 53%, HPLC ~99%) as a white solid. Sample from the reaction mixture and standard samples for compounds 5 and 6 were applied to a commercial silica gel TLC plate which was run in petroleum ether/ethyl acetate=4:1 and visualized under UV$_{254}$ and/or using iodine treatment. The R$_f$ for 5 was ~0.55 while the R$_f$ for compound 6 was ~0.57. $^1$H-NMR (300 MHz, CDCl$_3$) δ 7.15-7.53 (m, 15H), 5.44 (d, J=5.7 Hz, 1H), 4.32 (d, J=5.7 Hz, 1H), 4.30 (d, J=15.6 Hz, 1H), 4.18 (d, J=15.6 Hz, 1H), 1.45 (s, 3H), 1.32 (s, 3H); $^{13}$C-NMR DEPT-135 (75 MHz, CDCl$_3$) δ 128.73, 128.11, 127.45, 79.34, 74.9, 64.33 (OCH$_2$—), 27.4, 26.81.

Example 6b

Solution of 5 in DCM was added to reactor, then PDC (1800 g) and molecular sieves (362 g) were added and the mixture stirred and warmed to 25° C. Ac$_2$O (274 g) was added at 25° C. over 0.5 h, and then stirred for 30 min. The mixture reached 36° C. in 10 min. then cooled to 25° C. and stirred for 1.5 hrs, until IPC showed full consumption of 5. The suspension filtered through silica (1.37 kg) pad and the filtrate was washed with brine (3.69 kg) and the organic phase concentrated in vacuum at 15±5° C. The residue was dissolved in MTBE (4.4 kg), active carbon (0.05 kg) was added and the suspension stirred for 2 hrs. Then filtered to afford solution of 6 in MTBE (4.84 kg) ready to use in the next reduction step.

Example 6c

Compound 5 (72.5 g, 130.7 mmol) was taken up in methylene chloride (725 mL, 10 V) and charged to a 2 L three-neck flask equipped with an overhead stirrer, a nitrogen inlet, a thermocouple, and molecular sieves (72.5 g). Acetic anhydride (24.7 mL, 2.0 eq) was added followed by pyridinium dichromate (54.1 g, 143.8 mmol, 1.1 eq). The reaction was stirred at room temperature for 3 h. The reaction mixture was filtered through 350 g silica gel. The dark-colored chromium salts remained on the silica plug. The silica plug was washed with 200 mL methylene chloride. The resulting filtrate was washed with saturated sodium bicarbonate solution (200 mL), and then washed with 200 mL saturated sodium thiosulfate. The color was removed. The organic layer was concentrated to an orange oil to afford compound 6. Approximately 72 g of crude material was collected in 59 A % purity.

Example 7a (3aS,4R,6aR)-5-iodo-2,2-dimethyl-6-((trityloxy)methyl)-4,6a-dihydro-3aH-cyclopenta[d][1,3]dioxol-4-ol (7)

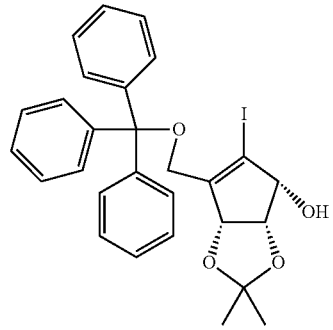 [SMILES: CC1(C)O[C@@H]2[C@H](O1)C(COC(c1ccccc1)(c1ccccc1)c1ccccc1)=C(I)[C@@H]2O]

Into a 500 L reactor was charged 100 L of methanol, followed by addition of 6 (9.7 kg) and CeCl$_3$·7H$_2$O (7.2 kg) in 1 kg portions over 0.5 hour. Temperature of the reaction mixture rose ~5° C. during the addition. The reaction mixture was cooled down to −10° C., and NaBH$_4$ (0.77 kg) was added in portions (~150 g) over 1 hour resulting in strong H$_2$ evolution with elevation of the reaction temperature. The transparent reaction mixture was then stirred for 2 hours at 0° C. until HPLC indicated complete conversion. Then 150 L of brine were added to result in white precipitates. The suspension was concentrated under vacuum to remove most of methanol and ethyl acetate (100 L) was added to the resulting residue and the mixture was stirred for 30 minutes. Then the organic layer was separated washed with brine (20 L) and dried over sodium sulfate, filtered and concentrated to dryness, and the residue was used directly in the next step. Sample from the reaction mixture and standard samples for compounds 6 and 7 were applied to a commercial silica gel TLC plate, with petroleum ether/ethyl acetate=4:1 as the mobile phase. 6 and 7 can be detected under UV$_{254}$ or visualized using iodine treatment. The R$_f$ for 6 was ~0.55 while the R$_f$ for compound 7 was ~0.57; $^1$H-NMR (300 MHz, CDCl$_3$) δ 7.21-7.48 (m, 15H), 5.20 (d, J=5.7 Hz, 1H), 4.77 (t, J=5.7 Hz, 1H), 4.39 (dd, J=5.4, 11.2 Hz, 1H), 3.90 (d, J=12.0 Hz, 1H), 3.79 (d, J=12.0 Hz, 1H), 2.81 (d, J=11.2 Hz, 1H), 1.43 (s, 3H), 1.32 (s, 3H); $^{13}$C-NMR DEPT-135 (75 MHz, CDCl$_3$) δ 128.79, 127.89, 127.11, 82.91, 78.14, 76.48, 62.58 (OCH$_2$—), 27.54, 27.11.

Example 7b

A solution of compound 6 (from Example 6b) was added to the reactor and cooled to 0° C. 2.2 kg MeOH was added followed by addition of CeCl$_3$·7H$_2$O (355 g) and the mixture stirred for 1 h to result homogeneous solution. NaBH$_4$ (8.8 g) was added in portions at 0° C., stirred for 30 min, IPC showed the reaction started and additional NaBH$_4$ (30 g) was added in portions with stirring for 1 h at 0° C. IPC showed complete consumption of compound 6. Saturated NH$_4$Cl (0.27 kg) was added followed by celite (266 g) and the mixture stirred for 30 min after which it was filtered, washed with water (12 L×3), and dried over Na$_2$SO$_4$ to give compound 7 in MTBE solution (5.5 kg), which was concentrated (below 40° C.) to furnish a residue. DMF (3 kg) was added and the solution was used directly in the next step.

Example 8a tert-butyl(((3aR,4R,6aR)-5-iodo-2,2-dimethyl-6-((trityloxy)methyl)-4,6a-dihydro-3aH-cyclopenta[d][1,3]dioxol-4-yl)oxy)diphenylsilane (8)

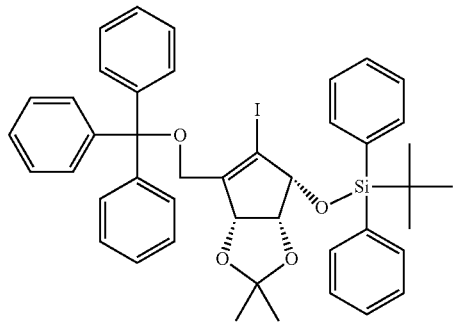 [SMILES: CC1(C)O[C@@H]2[C@H](O1)C(COC(c1ccccc1)(c1ccccc1)c1ccccc1)=C(I)[C@@H]2O[Si](c1ccccc1)(c1ccccc1)C(C)(C)C]

Into a 500 L reactor was charged DMF (100 L), Imidazole (3.6 kg) and crude compound 7 (from Example 7a, ~9.7 kg). The mixture was stirred at ambient temperature under nitrogen and t-BDPSCl (tert-butyldiphenyl chlorosilane) (1 kg) was added in portions over 1 hour. The reaction mixture was stirred 18 hours at ambient temperature. HPLC indicated complete conversion. Into the reactor was charged brine (100 L) and ethyl acetate (100 L) and the mixture was stirred for 30 minutes. The organic phase separated and the aqueous layer was extracted twice with 50 L of ethyl acetate. The combined ethyl acetate extract was washed twice with water (30 L) and concentrated under vacuum to give a golden-colored residue (~15.2 kg). The residue was diluted with 20 L of methanol and the mixture was stirred 1 hour at ambient temperature. The white precipitates were collected by filtration and dried in a vacuum oven (<40° C.) to afford compound 8 (8.3 kg, yield 60%, purity ~99%) as a white solid. Sample from the reaction mixture and standard samples for compounds 7 and 8 were applied to a commercial silica gel TLC plate, and the plate was developed in the mobile phase petroleum ether/ethyl acetate=10:1. Compounds 7 and 8 can be detected under $UV_{254}$. They can also be visualized using iodine treatment. The $R_f$ for 7 was ~0.1. The $R_f$ for compound 8 was ~0.9. $^1$H-NMR (300 MHz, $CDCl_3$) δ 7.18-7.82 (m, 25H), 4.94 (d, J=5.6 Hz, 1H), 4.47 (d, J=5.6 Hz, 1H), 4.05 (t, J=5.6 Hz, 1H), 3.89 (d, J=12.0 Hz, 1H), 3.78 (d, J=12.0 Hz, 1H), 1.29 (s, 3H), 1.26 (s, 3H), 1.13 (s, 9H); $^{13}$C-NMR DEPT-135 (75 MHz, $CDCl_3$, δ<100) δ 82.68, 78.96, 76.63, 62.78, 27.50, 27.11.

Example 8b

Imidazole (133.6 g) was added to solution of compound 7 (from Example 7b, KF:0.14%) and t-BDPSCl (448.5 g) was added drop-wise at 20-25° C. and the mixture was stirred for 14 hrs after which time it was added drop wise into 12 kg of water below 25° C. then stirred for 30 min. Ethyl acetate (5.8 kg) was added, the organic phase separated and the aqueous layer was extracted with ethyl acetate (2.9 kg×2). The combined organic phase was washed with brine (2.9 kg×2), dried and then concentrated below 45° C.

EtOH (600 g) was added and the mixture was heated to 30° C. to give a solution from which a solid precipitated out within 10 min. The mixture was stirred at 15° C. for 2 hrs and the solid filtered. The cake was washed with EtOH (50 g×2) to give a white solid which was dried in vacuum at 45° C. for 20 hrs to give 400 g of compound 8.

Example 9a tert-butyl(((3aR,4R,6aR)-5-fluoro-2,2-dimethyl-6-((trityloxy)methyl)-4,6a-dihydro-3aH-cyclopenta[d][1,3]dioxol-4-yl)oxy)diphenylsilane (9)

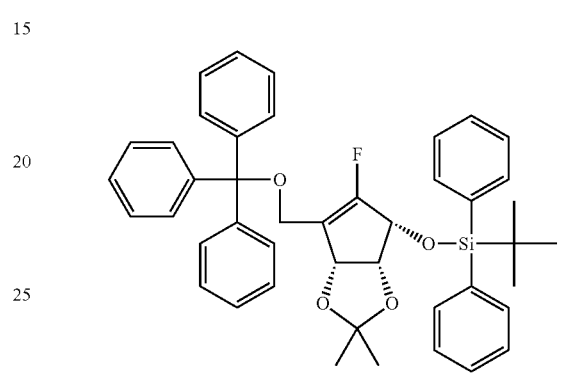

Compound 8 (0.48 kg) and NFSI (N-fluorobenzenesulfonimide) (0.29 kg) was dissolved in THF (3 L) and ether (1 L). To the solution was added 1.5 L of n-pentane, and the mixture was cooled to −78° C. in a dry-ice bath. A solution of n-BuLi in THF (2.5 M, 0.72 L) was added drop wise to the reaction mixture within 4 hours, while keeping the reaction temperature below −70° C. The reaction mixture was stirred another hour until HPLC indicated complete consumption of compound 8. Saturated ammonium chloride solution (aqueous, 2 L) was added drop wise to the reaction mixture. It was then allowed to warm to ambient temperature. Eight such reactions were combined and diluted with 30 L of ethyl acetate. The mixture was stirred for 30 minutes, then the organic phase separated and the aqueous layer was extracted with 20 L of ethyl acetate. The combined organic phase was washed with brine (10 L), dried over sodium sulfate, and concentrated to dryness. HPLC indicated ratio of compound 9 to its corresponding de-fluoro side product was about 3/1. The residue was loaded on a silica gel column (300-400 mesh) and eluted with petroleum ether/dichloromethane/ethyl acetate (first 100/0/0, then 200/10/1 to remove the front impurities, then changed to 200/15/1 to collect the desired product 9, (then 200/20/1 to collect the side product). Altogether 1.38 kg of compound 9 (yield 36%, purity ~95%) was obtained. $^1$H-NMR (300 MHz, $CDCl_3$) δ 7.25-7.92 (m, 25H), 5.04 (t, J=7.2 Hz, 1H), 4.45 (m, 1H), 4.33 (m, 1H), 3.98 (d, J=12.0 Hz, 1H), 3.86 (d, J=12.0 Hz, 1H), 1.55 (s, 3H), 1.48 (s, 3H), 1.18 (s, 9H); $^{13}$C-NMR DEPT-135 (75 MHz, $CDCl_3$, δ<100) δ 78.70, 75.35, 71.10, 56.39, 28.04, 27.25, 26.82.

Example 9b

Compound 8 (1.53 kg) and NFSI (1.64 kg) were dissolved in a mixture of THF/Hexane/MTBE and the mixture was stirred at room temperature for 5 minutes to form a clear solution. Then the solution was cooled to −65° C. with dry-ice bath (in acetone) under $N_2$ atmosphere. More solids precipitated during the cooling down and the solution became turbid. At ~−65° C., n-BuLi was added drop wise into the mixture. The reaction temperature needed strict monitoring and was kept at −55~−65° C. The addition of n-BuLi lasted for 4 h. (During the addition of n-BuLi (about 40% of the amount), a large amount of solid precipitated. That blocked the stirring.) After the addition of n-BuLi, the solution was stirred at about −60° C. for 0.5 h. TLC and HPLC showed complete consumption of compound 8. The solution was quenched with sat. $NH_4Cl$ (3 L), then the dry-ice bath was removed. Water (6 L) was added slowly to the mixture, which was stirred at room temperature for 30 minutes. Then the solution was allowed to stand for 15 minutes to separate into two layers. The organic layer was separated (10.3 kg). The aqueous layer was extracted with ethyl acetate (1.8 kg×1). Five such reactions were combined and the combined organic phase of the five batches were washed with brine, and dried over $Na_2SO_4$ (55 kg total based on Assay the product weight was 3.4 kg). Silica gel (300-400 mesh, 8 kg, 1.3 eq. (based on 8, wt./wt.)) and TEA (0.003 eq. (based on silica gel, wt./wt.)) were added to the crude product (about 8 kg) solution and the mixture was evaporated to dryness at ~35° C. and was loaded on a column (diameter: 45 cm; height: ~130 cm; silica gel: 300-400 mesh, 60 kg, 10 eq. (based on 8, wt./wt.); TEA: 0.003 eq. (based on silica gel, wt./wt.); eluent: PE/EA=200/1-150/1). During column chromatography, the fractions (plastic buckets (5 L)) were strictly monitored by TLC/HPLC. According to TLC/HPLC data, different parts were collected and concentrated respectively. The resulting solids from chromatography with different purity were slurried with heptane (3 v, stirred at 20-25° C. for 0.5 h) first to remove some of low polarity impurities, and then recrystallized with 6.6 v of iPrOH/heptane (10/1, v/v). The mixed solvent was added to crude solid product, and the mixture was heated at 85° C. to refluxing until the solid dissolved completely, then the heating bath was removed, the solution was cooled to 20-25° C. automatically under stirring, and was stirred for another 1-2 h at this temperature. The resulting solid was filtered and monitored by HPLC. Normally 2-3 (or more) recrystallizations were needed to reach purity of ≥97.0% of 9 and des-fluoro impurity <0.5% area (by HPLC, note: the recrystallization was effective to minimize des-fluoro impurity)).

Example 9c

Selective fluorination of compound 8 was performed through a boronic acid intermediate. Boronic acid intermediates were prepared from compound 8 by the following boronate reactions, Examples 9c-1 through 9c-3.

Example 9c-1

[(3aR,6S,6aR)-6-[tert-butyl(diphenyl)silyl]oxy-2,2-dimethyl-4-(trityloxymethyl)-6,6a-dihydro-3aH-cyclopenta[d][1,3]dioxol-5-yl]boronic acid (compound 9c-1)

To a 100 mL round-bottom 3-neck flask equipped with nitrogen inlet/outlet, stir bar, and thermocouple with temperature controller was charged 3.0877 g of compound 8 (3 mmol, 1.0 eq) and 30 mL tetrahydrofuran (10 V). Reaction was cooled to 0° C. To this solution was added 6.98 mL (9 mmol, 2.4 eq) of isopropylmagnesium chloride lithium chloride complex, 1.3 M in THF slowly over 15 minutes. The reaction was stirred at 0° C. for 1 hour. An HPLC assay indicated the formation of intermediate. 1.05 mL of trimethylborate (9 mmol, 2.5 eq) was added to the reaction. An HPLC assay after 1 hour at 0° C. indicated that the reaction was completed. Quenched reaction with saturated aqueous ammonium chloride solution (3V). The ice bath was removed and the reaction was warmed to room temperature. The reaction was charged with DI water (3V) and ethyl acetate (6V). The layers were separated and the aqueous layer was back-extracted with ethyl acetate (6V). The organic phases were combined and washed with brine (3V) and dried over $MgSO_4$. The resulting mixture was filtered. The filtrate was concentrated to dryness with a rotary evaporator. Obtained 2.87 grams (100% crude yield), 96 A % purity of [(3aR,6 S,6aR)-6-[tert-butyl(diphenyl)silyl]oxy-2,2-dimethyl-4-(trityloxymethyl)-6,6a-dihydro-3aH-cyclopenta[d][1,3]dioxol-5-yl]boronic acid (compound 9c-1).

Example 9c-2

[(3aR,6S,6aR)-2,2-dimethyl-5-(4,4,5,5-tetramethyl-1,3,2-dioxaborolan-2-yl)-4-(trityloxymethyl)-6,6a-dihydro-3aH-cyclopenta[d][1,3]dioxol-6-yl]oxy-tert-butyl-diphenyl-silane (9c-2)

To a 25 mL round-bottom 3-neck flask equipped with nitrogen inlet/outlet, stir bar, and thermocouple with temperature controller was charged 0.2806 g of compound 8 (0.353 mmol, 1.0 eq) and 3 mL tetrahydrofuran (10 V). The reaction was cooled to 0° C. To this solution was added 0.653 mL (0.847 mmol, 2.4 eq) of isopropylmagnesium chloride lithium chloride complex, 1.3 M in THF slowly over 15 minutes. The reaction was stirred at 0° C. for 1 hour. HPLC assay indicated formation of intermediate. 0.128 mL of 4,4,5,5 tetramethyl-1,3,2 dioxaborolane (0.884 mmol, 2.5 eq) was added to the reaction. An HPLC assay after 1 hour at 0° C. indicated that the reaction was completed. The reaction was quenched with saturated aqueous ammonium chloride solution (3V). The ice bath was removed and the reaction warmed to room temperature. The reaction was charged with DI water (3V) and ethyl acetate (6V). The layers were separated and the aqueous layer was back-extracted with ethyl acetate (6V). The organic phases were combined and washed with brine (3V) and dried over $MgSO_4$. The resulting mixture was filtered. The filtrate was concentrated to dryness by the rotary evaporator. Obtained 0.098 grams as a white solid, (35% yield), 80 A % purity of [(3aR,6S,6aR)-2,2-dimethyl-5-(4,4,5,5-tetramethyl-1,3,2-dioxaborolan-2-yl)-4-(trityloxymethyl)-6,6a-dihydro-3aH-cyclopenta[d][1,3]dioxol-6-yl]oxy-tert-butyl-diphenyl-silane (compound 9c-2).

Example 9c-3

[(3aR,6S,6aR)-6-[tert-butyl(diphenyl)silyl]oxy-2,2-dimethyl-4-(trityloxymethyl)-6,6a-dihydro-3aH-cyclopenta[d][1,3]dioxol-5-yl]boronic acid (9c-1) using ligand: To a 100 mL round-bottom 3-neck flask equipped with nitrogen inlet/outlet, stir bar, and thermocouple with temperature controller was charged 0.2272 g of compound 8 (0.286 mmol, 1.0 eq) and 3 mL tetrahydrofuran (THF). The reaction was cooled to 0° C. To this solution was added 0.528 mL (0.686 mmol, 2.4 eq) of isopropylmagnesium chloride lithium chloride complex, 1.3 M in THF slowly over 15 minutes. The reaction was stirred at 0° C. for 1 hour. Added 0.065 mL (0.343 mmol, 1.2 eq) of Bis[2-(N,N-dimethylamino)ethyl] ether. An HPLC assay indicated the formation of intermediate. 1.05 mL of trimethylborate (0.009 mmol, 2.5 eq) was added to the reaction. The ice bath was removed and the reaction allowed to warm to room temperature for 30 minutes. An HPLC assay indicated that the reaction was complete. The reaction was cooled to 0° C. The reaction was quenched with saturated aqueous ammonium chloride solution (3V). The ice bath was removed and the reaction was warmed to room temperature. The reaction was charged with DI water (3V) and ethyl acetate (6V). The layers were separated and the aqueous layer was back-extracted with ethyl acetate (6V). The organic phases were combined and washed with brine (3V) and dried over MgSO$_4$. The resulting mixture was filtered. The filtrate was concentrated to dryness with a rotary evaporator. Obtained 0.077 grams as a white solid, (36% yield), and 100 A % purity of [(3aR,6S,6aR)-6-[tert-butyl(diphenyl)silyl]oxy-2,2-dimethyl-4-(trityloxymethyl)-6,6a-dihydro-3 aH-cyclopenta[d][1,3]dioxol-5-yl]boronic acid (compound 9c-1).

Example 9c-4

[(3aR,6R,6aR)-5-fluoro-2,2-dimethyl-4-(trityloxymethyl)-6,6a-dihydro-3aH-cyclopenta[d][1,3]dioxol-6-yl]oxy-tert-butyl-diphenyl-silane (compound 9)

To a 100 mL round bottom flask equipped with nitrogen inlet/outlet, stir bar, and thermocouple with temperature controller was charged 2.877 grams of boronic acid intermediate (for example, either compound 9c-1 or compound 9c-2) (3.89 mmol, 1.0 eq) in methyl-tert-butyl ether (6 V). In a separate flask was charged 0.186 grams sodium hydroxide flakes (4.67 mmol, 1.2 eq) and methanol (10V). The solution was stirred until all the sodium hydroxide went into solution. The sodium hydroxide/methanol solution was added to the boronic acid intermediate and the reaction was stirred at room temperature for 15 minutes. After 15 minutes the reaction was cooled to 0° C. 3.012 grams of silver trifluoromethane sulfonate (11.67 mmol, 3.0 eq) was added in one portion. The reaction turned brown. After 30 minutes HPLC showed all the starting boronic acid intermediate was consumed. The solvent was removed with a rotary evaporator using no heat on the water bath. Any residual methanol was coevaporated with acetone (2×5 V). Acetone (10 V) was added to the crude residue. 7.042 grams of 4 Å molecular sieves (2.5 wt) and 4.2312 grams of 1-chloromethyl-4-fluoro-1,4-diazoniabicyclo[2.2.2]octane bis(tetrafluoroborate) (Selectfluor®) (4.67 mmol, 3.0 eq) was added to the reaction. The reaction was stirred at room temperature for 1 hour. HPLC showed that the reaction was completed. The reaction was filtered through Celite® and concentrated on the rotary evaporator to obtain 2.07 grams (78% yield) of compound 9 as a white solid.

Example 10

(3aS,4R,6aR)-5-fluoro-2,2-dimethyl-6-((trityloxy)methyl)-4,6a-dihydro-3aH-cyclopenta[d][1,3]dioxol-4-ol (10)

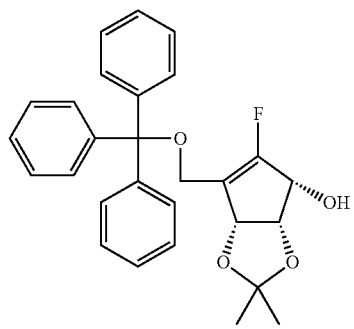 [SMILES: CC1(C)O[C@@H]2[C@H](O1)C(COC(c1ccccc1)(c1ccccc1)c1ccccc1)=C(F)[C@@H]2O]

Compound 9 (1370 g, 1 wt, 1 eq) was dissolved in THF (5.5 L, 4 vol). TBAF (tetra-n-butylammonium fluoride) 1.0 M in THF (2.20 L, 1.61 vol) was added in one portion (not exothermic) and the resulting solution stirred at 20 to 25° C. After 2 h, TLC analysis (70:30 heptanes:TBME (methyl tert-butyl ether) 7:3, KMnO$_4$ visualisation) indicated the reaction was complete by absence of starting material. The reaction mixture was concentrated to an oil under reduced pressure at 40° C. (water bath) on a rotary evaporator until solvent collection ceased. The residue was dissolved in TBME (11.0 L, 8 vol) and subsequently washed with water (2×4.1 L, 2×3 vol) and saturated sodium hydrogen carbonate (4.1 L, 3 vol). The organic phase was dried over Na$_2$SO$_4$ (1.37 kg, 1 wt), filtered and the cake washed with TBME (1.37 L×2, 2×1 vol). The combined filtrates were concentrated under reduced pressure at up to 40° C. (water bath) on a rotary evaporator until the TBME content was <5% w/w by $^1$H NMR to give 10 as a thick pale yellow/orange oil. $^1$H-NMR (400 MHz, CDCl$_3$) δ 7.7 ppm (d, 4H) TBDPS-F, 7.2-7.5 ppm, (m, 21H) Trityl and TBDPS-F, 5.1 ppm, (t, J=6.3 Hz, 1H) (CH), 4.7 ppm, (m, J=3.5 Hz, 1H) (CH), 4.4 ppm, broad (t, 6.3 Hz, 1H) (CH), 3.9 ppm, (d, J=11.9 Hz) 1H, 3.8 ppm, (d, J=9.9 Hz, 1.7 Hz, 1H) (CH$_2$), δ 2.8 ppm, (d, J=9.4 Hz, 1H) (OH), δ 1.48 ppm, s, 3H CH$_3$ Acetonide, δ 1.46 ppm, s, 3H CH$_3$ Acetonide, δ 1.1 ppm, s, 9H TBDPS-F (3×CH$_3$), Solvents δ 3.2 ppm, 1.2 ppm TBME, δ 3.7 ppm, 1.7 ppm THF.

Example 11

(3aR,4R,6aR)-5-fluoro-2,2-dimethyl-6-((trityloxy)methyl)-4,6a-dihydro-3aH-cyclopenta[d][1,3]dioxol-4-yl methanesulfonate (11)

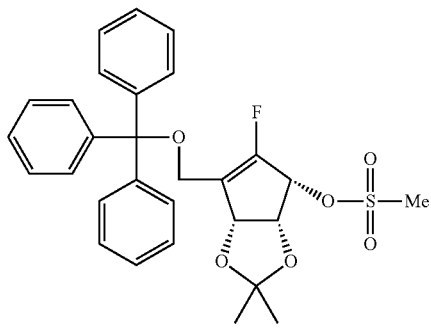 [SMILES: CC1(C)O[C@@H]2[C@H](O1)C(COC(c1ccccc1)(c1ccccc1)c1ccccc1)=C(F)[C@@H]2OS(C)(=O)=O]

Compound 10 (787 g (corrected), 1 wt), (gross input 1292 g), was dissolved in DCM (7.87 L, 10 vol) and cooled to 0 to 5° C. Triethylamine (368 mL, 0.468 vol, 1.5 eq) was charged followed by MsCl (164 mL, 0.208 vol, 1.3 eq) whilst maintaining the temperature at 0 to 5° C. IPC by $^1$H NMR analysis after 30 minutes indicated that 94.2% conversion had been achieved. An additional charge of triethylamine (28 mL) and MsCl (16 mL) (2 mol % per 1% conversion remaining) was made. IPC analysis after 30 minutes indicated that the conversion had increased to 97.3%. A second additional charge of triethylamine (13 mL) and MsCl (7.5 mL) was made. After a further 30 minutes IPC by $^1$H NMR analysis indicated that 100% conversion had been achieved. Water (7.87 L, 10 vol) was charged to the reaction and the mixture warmed to 15 to 25° C. Once the reaction was within the temperature range it was stirred for 10 minutes and the phases separated. The organic phase was returned to the flask, saturated NaHCO$_3$ (7.87 L, 10 vol) charged and the two phases mixed for 10 to 20 minutes, then separated. The organic phase was dried over Na$_2$SO$_4$ (787 g, 1 wt) for 10 minutes, filtered and the filter cake washed with DCM (2×787 mL, 2×1 vol). The combined filtrate and washes were concentrated at up to 30° C. on a rotary evaporator under vacuum to obtain 11 as an orange oil. $^1$H-NMR (400 MHz, CDCl$_3$) δ 7.7 ppm, d, 4H, TBDPS-F stage 1 by-product, δ 7.25 to 7.5 ppm, 21H. Trityl group and TBDPS-F by-product, δ 5.23 ppm, (d, J=5.8 Hz, 1H) (CH), δ 5.10 ppm, (t, J=7.1 Hz, 1H) (CH), δ 4.77 ppm, (m, J=2.8 Hz, 1H) (CH), δ 4.0 ppm, (d, J=12.6 Hz, 1H), 3.9 ppm, (d, J=12.6 Hz, 1H) (CH$_2$), δ 3.1 ppm, s, 3H, Mesylate, (CH$_3$), δ 1.4 ppm, 6H, Acetonide, (2×CH$_3$), δ 1.1 ppm, 3, 9H, (3×CH$_3$, TBDPSF), Solvents δ 5.8 ppm, s, 2H DCM.

Example 12

4-amino-1-((3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one (12)

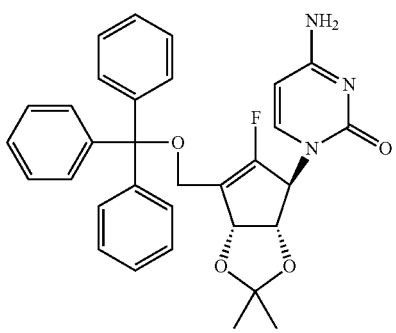 [SMILES: CC1(C)O[C@@H]2[C@H](O1)C(COC(c1ccccc1)(c1ccccc1)c1ccccc1)=C(F)[C@H]2n1ccc(N)nc1=O]

Cytosine (47.9 g, 0.42 wt, 2 eq) and cesium carbonate (141.4 g, 1.24 wt, 2 eq) were suspended in DMSO (684 mL, 6 vol) and heated to 40 to 45° C. After 75 minutes 11 (114 g, 1 wt, corrected, 1 eq) dissolved in DMSO (400 mL, 3.5 vol) was charged to the reaction followed by a line rinse of DMSO (57 mL, 0.5 vol) and the reaction temperature adjusted to 40 to 45° C. The temperature was maintained at the upper end of the temperature range at 44 to 45° C. for the duration of the reaction. Conversion by HPLC after 4 h was 60.9% increasing to 97.6% after 20 h and a pass result obtained of 99.0% after 23 h. The ratio of the N- to O-isomers was at 88:12. The reaction was cooled to room temperature and EtOAc (1140 mL, 10 vol) charged followed by water (1140 mL, 10 vol) maintaining the temperature below at 25° C. (water addition is exothermic). After stirring for 10 minutes the phases were allowed to settle for 10 minutes and then separated. The aqueous phase was re-extracted with EtOAc (1140 mL, 10 vol) by stirring for 10 minutes and again allowing too settle for 10 minutes before separating. The aqueous phase was checked by TLC and HPLC for product content, which indicated that all the product had been recovered with the first two extracts. The organic extracts were combined. 3% w/w brine (3×570 mL, 3×5 vol) washes were performed mixing the organic extracts for 10 minutes and allowing a minimum 10 minutes for the phases to settle on ceasing prior to the separation. Analysis of each aqueous phase by HPLC indicated that very little/no product was being lost. A fourth wash was performed with water (5 vol). In each case the aqueous wash was very slightly hazy in appearance. After completion of the wash sequence the DMSO level has been reduced to 0.02% w/w vs. the N-alkyl product, below the targeted 0.15% w/w limit. The organic phase was dried over sodium sulfate (114 g, 1 wt) filtered and the filter cake washed with EtOAc (2×1 vol). The filtrates were concentrated at up to 40° C. (water bath) on a rotary evaporator to give crude 12 as an orange foam 175.1 g. $^1$H NMR analysis gave the following composition: 12 56.4% w/w, O-alkyl side product 7.2% w/w, t-BDPSF (t-butyldiphenylsilylfluoride) 31.3% w/w and EtOAc 5.1% w/w, which equated to an approximate contained mass of 12 of 98 g. The crude material was purified by dry flash chromatography on silica (1.7 kg, 10 wt), complete separation of the isomers was obtained. The product fractions were concentrated at up to 40° C. (water bath) to give 12 as a pale brown foam 90.5 g, 77.2% th (corrected by $^1$H NMR assay). The chemical purity by HPLC was 97.8% area. The chromatography was performed using 4 dry flash columns per batch of crude material (4×~170 g) each using 1.7 kg (10 wt) of silica. The crude product was loaded in approximately 1 vol of DCM and then eluted using the gradient: 1×DCM, 9×1% MeOH/DCM, 10×2% MeOH/DCM, 10×6% MeOH/DCM. Clean separation of the stage 1 by-product and O-alkyl isomer from 12 was achieved. The product fractions were concentrated on a rotary evaporator at up to 40° C. to obtain an orange foam. Concentration was continued until the DCM content was <10% w/w. $^1$H-NMR (400 MHz, CDCl$_3$), δ 8.7 ppm, s broad, 1H, δ 7.2 to 7.5 ppm, m, 16H, δ 6.7 ppm, (d, J=7.3 Hz, 1H) (CH), δ 6.6 ppm, broad s, 1H, δ 5.5 ppm, (d, J=7.4 Hz, 1H) (CH), δ 5.4 ppm, (t, J=5.6 Hz, 1H) (CH), δ 4.9 ppm, broad s, 1H, (CH), δ 4.7 ppm, broad s, 1H, (CH), δ 3.9 ppm, (d, J=12.1 Hz, 1H), 3.8 ppm, (d, J=12.1 Hz, 1H) (CH2), δ 1.48 ppm, s, 3H (CH3), δ 1.41 ppm, s, 3H (CH3), Solvents δ 5.3 ppm, s, 2H DCM.

This reaction from 11 to 12 is a general reaction, forming 12 with high regio- and stereoselectivity, which is, for example, useful for coupling cytosine and other nucleotide bases. This reaction has not previously been reported. For example, this reaction can be used with other reactants and products.

Example 13

4-amino-1-((1S,4R,5S)-2-fluoro-4,5-dihydroxy-3-(hydroxymethyl)cyclopent-2-en-1-yl)pyrimidin-2(1H)-one (13)

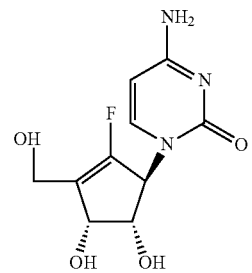 [SMILES: Nc1ccn([C@@H]2C(F)=C(CO)[C@@H](O)[C@H]2O)c(=O)n1]

Compound 12 (720 g, 1 wt) was charged to a flask followed by methanol (3.6 L, 5.0 vol) which formed a suspension. 2 M HCl (734 mL, 1.02 vol, 1.1 eq) was added which gave a hazy solution. The mixture was heated to reflux (68 to 69° C.), after 1 h IPC by 1H NMR indicated that the trityl deprotection was complete and that removal of the acetonide had reached 89%. Distillation was started and the distillate collected in 1 volume portions. After the removal of 1 volume of distillate, 1 volume of 95:5 methanol:water was added. Each distillation required 40 to 50 minutes to complete. After 2 cycles 97.5% conversion was achieved. After a further 3 distillation cycles conversion by HPLC was 99.6%; one further distillation was performed which increased the conversion to 99.8%. The overall reaction time was 5.5 h. The reaction was allowed to cool, the trityl by-product, whilst initially forming an oil, crystallised once the temperature reached ~40° C., the slurry was allowed to cool to room temperature overnight. The slurry was filtered and washed with water (2×1 vol), the combined filtrates were concentrated on a rotary evaporator at up to 40° C. until the methanol was removed (2.75 h). An aqueous solution of the product ~1.5 L was obtained which had some precipitate present (remaining trityl by-product). Additional water, 3 L, was added to raise the overall volumes to approximately 6. The aqueous solution was extracted with TBME (2×2.1 L, 2×3 vol) to remove the remaining trityl by-product. The pH of the aqueous solution was subsequently adjusted from 1.13 to 9.89 with Ambersep 900 (OH form) resin (pre prepared) 650.2 g. After stirring for 40 minutes the pH was unchanged. The slurry was filtered (Glass microfibre) and washed with water (1.08 L, 1.5 vol). The resulting aqueous solution was washed with TBME twice and the pH adjusted with the pre-prepared Ambersep 900 resin. (~0.8 wt) of resin was required to raise the pH from 1.36 to 10.47. After filtration the filter-cake was subsequently slurried in methanol (5 volumes) for 1 hour and the filtrates combined with the product filtrate. Concentration of this water/methanol product solution followed by oven drying the resulting residue under high vacuum (for 72 hrs.) gave the crude product (299.6 g, 87.5%) as a yellow solid which could be crystallized as follows: crude 13 (1.0 wt) and methanol (4.5 vol) were stirred under nitrogen and the resulting suspension was heated to 60 to 65° C. and then cooled to 50 to 55° C. and clarified through a glass microfiber filter followed by a line rinse of methanol (0.25 vol). The clarified solution was cooled gradually to 20 to 25° C. over 1 to 1.5 hour. Once the flask contents were within the temperature range and crystallisation has initiated filtered ethanol (4.75 vol) was charged over at least 45 minutes whilst maintaining the temperature at 20 to 25° C. The resulting slurry was cooled to 0 to 5° C. and then aged for at least 15 hours at 0 to 5° C. to give pure 13 which was filtered as an off-white to yellow solid (in a yield of 65 to 95% w/w.). $^1$H-NMR (400 MHz, DMSOd$_6$), δ 7.40 ppm, (d, J=7.3 Hz, 1H) CH cytosine, δ 7.20 ppm, (broad d, J=9.1 Hz, 2H) NH$_2$, δ 5.74 ppm, (d, J=7.3 Hz, 1H) CH cytosine, δ 5.30 ppm, broad s, 1H, CH, δ 5.15 ppm, (d, J=7.1 Hz, 1H) (OH), δ 5.00 ppm, (d, J=6.1 Hz, 1H) (OH), δ 4.80 ppm, (q, J=5.3 Hz, 1H)(OH), δ 4.48 ppm, (q, J=5.3 Hz, 1H) CH, δ 4.17 ppm, (dd, J=9.1 Hz, 3.8 Hz, 1H) CH, δ 4.13 ppm, (dt, J=6.1 Hz, 5.8 Hz, 1H) CH, δ 3.91 ppm, (broad d, J=12.9 Hz, 2.8 Hz, 1H) CH.

All documents (including patent applications, published patent applications, and patents) cited herein or cited in any one of the patent applications, published patent applications, and patents incorporated by reference are hereby incorporated by reference in their entirety and as if each had been individually incorporated.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is, therefore, to be understood that, within the scope of the claims and their equivalents, the invention may be practiced otherwise than as specifically described.

The invention claimed is:

1. A process for the preparation of (1R,4S,5S)-2-iodo-4,5-isopropylidenedioxy-1-(trityloxymethyl)cyclopent-2-enol (5) from (3aR,6aR)-2,2-dimethyl-6-((trityloxy)methyl)tetrahydrofuro[3,4-d][1,3]dioxol-4-ol (2), comprising:
   reacting (3aR,6aR)-2,2-dimethyl-6-((trityloxy)methyl) tetrahydrofuro[3,4-d][1,3]dioxol-4-ol (2) with iodoform to form 1-((4R,5S)-5-(2,2-diiodovinyl)-2,2-dimethyl-1,3-dioxolan-4-yl)-2-(trityloxy)ethanol (3).

2. The process of claim 1, further comprising:
   oxidizing 1-((4R,5S)-5-(2,2-diiodovinyl)-2,2-dimethyl-1,3-dioxolan-4-yl)-2-(trityloxy)ethanol (3) to form 1-((4S,5S)-5-(2,2-diiodovinyl)-2,2-dimethyl-1,3-dioxolan-4-yl)-2-(trityloxy)ethanone (4).

3. The process of claim 2, wherein the step of oxidizing 1-((4R,5S)-5-(2,2-diiodovinyl)-2,2-dimethyl-1,3 -dioxolan-4-yl)-2-(trityloxy)ethanol (3) to form 1-((4S,5S)-5-(2,2-diiodovinyl)-2,2-dimethyl-1,3-dioxolan-4-yl)-2-(trityloxy) ethanone (4) comprises Swern oxidation with diisopropylcarbodiimide, pyridine, trifluoroacetic acid (CF3COOH), and sodium hypochlorite (NaOCl ).

4. The process of claim 2, further comprising:
   reacting 1-((4S,5S)-5-(2,2-diiodovinyl)-2,2-dimethyl-1,3-dioxolan-4-yl)-2-(trityloxy)ethanone (4) with n-BuLi to form (1R,4S,5S)-2-iodo-4,5-isopropylidenedioxy-1-(trityloxymethyl)cyclopent-2-enol (5).

5. The process of claim 1, further comprising:
   oxidizing 1-((4R,5S)-5-(2,2-diiodovinyl)-2,2-dimethyl-1,3-dioxolan-4-yl)-2-(trityloxy)ethanol (3) to form 1-((4S,5S)-5-(2,2-diiodovinyl)-2,2-dimethyl-1,3-dioxolan-4-yl)-2-(trityloxy)ethanone (4); and
   reacting 1-((4S,5S)-5-(2,2-diiodovinyl)-2,2-dimethyl-1,3-dioxolan-4-yl)-2-(trityloxy)ethanone (4) with n-BuLi to form (1R,4S,5S)-2-Iodo-4,5-isopropylidenedioxy-1-(trityloxymethyl)cyclopent-2-enol (5).

6. A process for the preparation of 1-((4R,5S)-5-(2,2-diiodovinyl)-2,2-dimethyl-1,3-dioxolan-4-yl)-2-(trityloxy) ethanol (3), comprising:
   reacting (3aR,6aR)-2,2-dimethyl-6-((trityloxy)methyl) tetrahydrofuro[3,4-d][1,3]dioxol-4-ol (2) with iodoform to form 1-((4R,5S)-5-(2,2-diiodovinyl)-2,2-dimethyl-1,3-dioxolan-4-yl)-2-(trityloxy)ethanol (3).

7. A process for the preparation of 4-amino-1-((1S,4R,5S)-2-fluoro-4,5-dihydroxy -3-(hydroxymethyl)-cyclopent-2-en-1-yl)-pyrimidin-2(1H)-one (13), comprising:
   reacting (3aR,6aR)-2,2-dimethyl-6-((trityloxy)methyl) tetrahydrofuro[3,4-d][1,3]dioxol-4-ol (2) with iodoform to form 1-((4R,5S)-5-(2,2-diiodovinyl)-2,2-dimethyl-1,3-dioxolan-4-yl)-2-(trityloxy)ethanol (3); and
   isolating 4-amino-1-((1S,4R,5S)-2-fluoro-4,5-dihydroxy-3-(hydroxymethyl)-cyclopent-2-en-1-yl)-pyrimidin-2(1H)-one(13).

8. The process of claim 7, further comprising:
   oxidizing 1-((4R,5S)-5-(2,2-diiodovinyl)-2,2-dimethyl-1,3-dioxolan-4-yl)-2-(trityloxy)ethanol (3) to form 1-((4S,5S)-5-(2,2-diiodovinyl)-2,2-dimethyl-1,3-dioxolan-4-yl)-2-(trityloxy)ethanone (4).

9. The process of claim 8, wherein the step of oxidizing 1-((4R,5S)-5-(2,2-diiodovinyl)-2,2-dimethyl-1,3-dioxolan-4-yl)-2-(trityloxy)ethanol (3) to form 1-((4S,5S)-5-(2,2-diiodovinyl)-2,2-dimethyl-1,3-dioxolan-4-yl)-2-(trityloxy)

ethanone (4) comprises Swern oxidation with diisopropylcarbodiimide, pyridine, trifluoroacetic acid (CF3COOH), and sodium hypochlorite (NaOCl).

10. The process of claim 8, further comprising:
reacting 1-((4S,5S)-5-(2,2-diiodovinyl)-2,2-dimethyl-1,3-dioxolan-4-yl)-2-(trityloxy)ethanone (4) with n-BuLi to form (1R,4S,5S)-2-iodo-4,5-isopropylidenedioxy-1-(trityloxymethyl)cyclopent-2-enol (5).

11. The process of claim 10, further comprising:
oxidizing (1R,4S,5S)-2-iodo-4,5-isopropylidenedioxy-1-(trityloxymethyl)cyclopent-2-enol (5) to form (3aR,6aR)-5-iodo-2,2-dimethyl-6-((trityloxy)methyl)-3aH-cyclopenta[d][1,3]dioxol-4(6aH)-one(6).

12. The process of claim 7, further comprising:
oxidizing 1-((4R,5S)-5-(2,2-diiodovinyl)-2,2-dimethyl-1,3-dioxolan-4-yl)-2-(trityloxy)ethanol (3) to form 1-((4S,5S)-5-(2,2-diiodovinyl)-2,2-dimethyl-1,3-dioxolan-4-yl)-2-(trityloxy)ethanone (4); and
reacting 1-((4S,5S)-5-(2,2-diiodovinyl)-2,2-dimethyl-1,3-dioxolan-4-yl)-2-(trityloxy)ethanone (4) with n-BuLi to form (1R,4S,5S)-2-Iodo-4,5-isopropylidenedioxy-1-(trityloxymethyl)cyclopent-2-enol (5).

13. The process of claim 7, further comprising:
reacting 4-amino-1-(3aS,4S,6aR)-5-fluoro-2,2-dimethyl-6-((trityloxy)methyl)-4,6a-dihydro-3aH-cyclopenta[d][1,3]dioxol-4-yl) pyrimidin-2(1H)-one(12) with an acid to form 4-amino-1-((1S,4R,5S)-2-fluoro-4,5-dihydroxy-3-(hydroxymethyl)-cyclopent-2-en-1-yl)-pyrimidin-2(1H)-one (13).

14. The process of claim 13, further comprising:
reacting (3aR,4R,6aR)-5-fluoro-2,2-dimethyl-6-((trityloxy)methyl)-4,6a-dihydro-3aH-cyclopenta[d][1,3]dioxol-4-yl methanesulfonate(11) with cytosine to form 4-amino-1-(3aS,4S,6aR)-5-fluoro-2,2-dimethyl-6-((trityloxy)methyl)-4,6a-dihydro-3aH-cyclopenta[d][1,3]dioxol-4-yl) pyrimidin-2(1H)-one(12).

15. The process of claim 14, further comprising:
reacting (3aS,4R,6aR)-5-fluoro-2,2-dimethyl-6-((trityloxy)methyl)-4,6a-dihydro-3aH-cyclopenta[d][1,3]dioxol-4-ol(10) with MsCl to form (3aR,4R,6aR)-5-fluoro-2,2-dimethyl-6-((trityloxy)methyl)-4,6a-dihydro-3aH-cyclopenta[d][1,3]dioxol-4-yl methanesulfonate (11).

16. The process of claim 13, further comprising:
reacting (3aS,4R,6aR)-5-fluoro-2,2-dimethyl-6-((trityloxy)methyl)-4,6a-dihydro-3aH-cyclopenta[d][1,3]dioxol-4-ol(10) with MsCl to form (3aR,4R,6aR)-5-fluoro-2,2-dimethyl-6-((trityloxy)methyl)-4,6a-dihydro-3aH-cyclopenta[d][1,3]dioxol-4-yl methanesulfonate(11); and
reacting (3aR,4R,6aR)-5-fluoro-2,2-dimethyl-6-((trityloxy)methyl)-4,6a-dihydro-3aH-cyclopenta[d][1,3]dioxol-4-yl methanesulfonate (11) with cytosine to form 4-amino-1-(3aS,4S,6aR)-5-fluoro-2,2-dimethyl-6-((trityloxy)methyl)-4,6a-dihydro-3aH -cyclopenta[d][1,3]dioxol -4-yl)pyrimidin-2(1H)-one(12).

* * * * *